United States Patent
Sonnenschein et al.

(10) Patent No.: US 7,530,984 B2
(45) Date of Patent: May 12, 2009

(54) TRANSGASTRIC METHOD FOR CARRYING OUT A PARTIAL FUNDOPLICATION

(75) Inventors: Elazar Sonnenschein, Beer Sheva (IL); Amir Govrin, Tel Aviv (IL); Minelu Sonnenschein, Meitar (IL)

(73) Assignee: Medigus Ltd., Omer (IL)

( * ) Notice: Subject to any disclaimer, the term of this patent is extended or adjusted under 35 U.S.C. 154(b) by 468 days.

(21) Appl. No.: 11/446,740

(22) Filed: Jun. 5, 2006

(65) Prior Publication Data

US 2007/0282356 A1  Dec. 6, 2007

(51) Int. Cl.
*A61B 17/10* (2006.01)

(52) U.S. Cl. .................. 606/139; 128/898; 606/191; 606/192

(58) Field of Classification Search ............ 606/139, 606/191–192; 128/898
See application file for complete search history.

(56) References Cited

U.S. PATENT DOCUMENTS

| | | | | |
|---|---|---|---|---|
| 529,837 | A * | 11/1894 | Quimby | 418/202 |
| 5,382,231 | A * | 1/1995 | Shlain | 128/898 |
| 5,403,326 | A * | 4/1995 | Harrison et al. | 606/139 |
| 5,558,665 | A | 9/1996 | Kieturakis | |
| 5,571,116 | A * | 11/1996 | Bolanos et al. | 606/139 |
| 5,603,443 | A * | 2/1997 | Clark et al. | 227/178.1 |
| 5,676,674 | A | 10/1997 | Bolanos et al. | |
| 5,787,897 | A | 8/1998 | Kieturakis | |
| 5,897,562 | A | 4/1999 | Bolanos et al. | |
| 6,113,609 | A * | 9/2000 | Adams | 606/139 |
| 6,159,146 | A * | 12/2000 | El Gazayerli | 600/106 |
| 6,302,311 | B1* | 10/2001 | Adams et al. | 227/176.1 |
| 6,312,437 | B1* | 11/2001 | Kortenbach | 606/139 |
| 6,338,737 | B1* | 1/2002 | Toledano | 606/219 |
| 6,736,828 | B1* | 5/2004 | Adams et al. | 606/213 |
| 7,204,842 | B2* | 4/2007 | Geitz | 606/142 |
| 7,347,863 | B2* | 3/2008 | Rothe et al. | 606/139 |
| 2001/0054636 | A1* | 12/2001 | Nicolo | 227/175.1 |
| 2002/0068946 | A1* | 6/2002 | Kortenbach et al. | 606/142 |

FOREIGN PATENT DOCUMENTS

| WO | WO 00/53102 | 9/2000 |
|---|---|---|
| WO | WO 02/24058 | 3/2002 |

(Continued)

OTHER PUBLICATIONS

The Esophagus, 3rd Ed., Donald O. Castell, Ed., pp. 515-517.

*Primary Examiner*—(Jackie) Tan-Uyen T Ho
*Assistant Examiner*—Son Dang
(74) *Attorney, Agent, or Firm*—Roach Brown McCarthy & Gruber, P.C.; Kevin D. McCarthy

(57) ABSTRACT

The invention is a transgastric method for the endoscopic partial fundoplication for the treatment of gastroesophageal reflux disease (GERD). The method makes use of an articulated endoscope, which is introduced through the mouth and esophagus into the stomach of the patient. A cutting tool is introduced through the working channel of the endoscope to cut a hole in the wall of the stomach. The endoscope is pushed through the hole and a grabbing tool is introduced through the working channel and used to grab the tissue at a location on the outer surface of the stomach and move the grabbed tissue close to the esophagus. The grabbed tissue is then stapled to the esophagus using a stapling device that is an integral part of the endoscope. If desired, after stapling the endoscope can be rotated one or more times and the procedure repeated. After the selected portions of the stomach wall have been attached to the esophagus, the endoscope is withdrawn from the body of the patient and the hole in the stomach wall is closed, preferably by means of a dedicated endoscopic stapling device especially designed for the task of closing holes in tissue.

19 Claims, 26 Drawing Sheets

FOREIGN PATENT DOCUMENTS

| | | |
|---|---|---|
| WO | WO 02/39909 | 5/2002 |
| WO | WO 01/67964 | 7/2002 |
| WO | WO 02/068988 | 9/2002 |
| WO | WO 2005/002210 | 1/2005 |
| WO | WO 2005/115221 | 12/2005 |
| WO | WO 2005/115255 | 12/2005 |
| WO | WO 2005/120329 | 12/2005 |
| WO | WO 2006/033109 | 3/2006 |

* cited by examiner

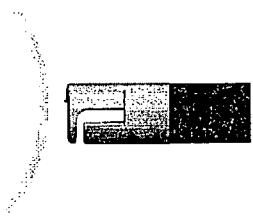 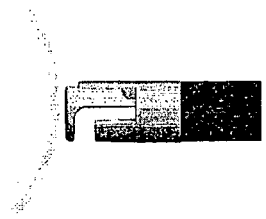 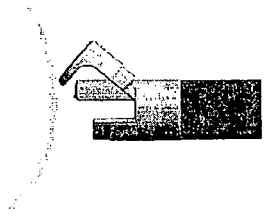
Fig. 20A　　　Fig. 20B　　　Fig. 20C
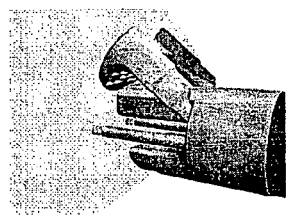 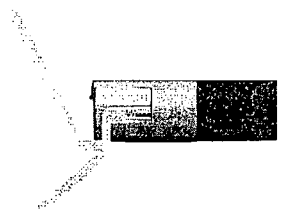 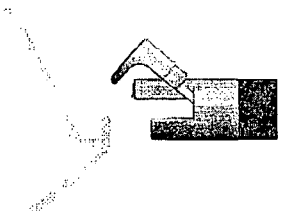
Fig. 20D　　　Fig. 20E　　　Fig. 20F

TRANSGASTRIC METHOD FOR CARRYING OUT A PARTIAL FUNDOPLICATION

FIELD OF THE INVENTION

The present invention relates to endoscopic system. More particularly, the invention relates to a transgastric method for the endoscopic partial fundoplication for the treatment of gastroesophageal reflux disease (GERD) and to an endoscopic system for carrying out the procedure.

BACKGROUND OF THE INVENTION

GERD is caused by abnormal regurgitation of acid fluids from the stomach into the esophagus. The stomach generates strong acids to aid digestion. The esophagus is normally protected from these acids by a one-way valve mechanism at its junction with the stomach. This one-way valve is called the lower esophageal sphincter (LES). In patients with GERD, the LES frequently malfunctions because it is either too weak or too short. The short or weak LES cannot retain the contents of the stomach as it fills up and pressure inside rises.

When the LES fails, acid flows backwards, i.e. refluxes, up into the esophagus which is not designed to handle it. The result is an acid burn, commonly called "heartburn", or "acid indigestion". Heartburn feels like a burning or pressure pain behind the breastbone, which may feel very much like a heart attack. When the acid is in the esophagus, and one belches, it may regurgitate up into the back of the throat, tasting sour or bitter, and causing a burning sensation. If this occurs at night, one may wake-up with either a hot, fiery feeling in the back of the throat, or even coughing and gasping resulting from acid entering the breathing tubes. This last phenomenon is called Reflux Nocturnal Aspiration and can be quite serious in itself.

Reflux Nocturnal Aspiration can be dangerous, because it introduces acid and bacteria into the airway and lungs. This can cause recurrent bronchitis, pneumonia, lung abscess, or chronic scarring of the lung. It can also lead to asthma attacks in those with an asthmatic tendency.

When acid reflux and its symptoms occur daily or up to three or four times weekly, the esophagus cannot withstand the damaging effects of the acid bath and becomes inflamed, especially at its lower part. Swallowing can frequently be painful, and food may stick in the chest. This is called reflux esophagitis, meaning inflammation of the esophagus due to acid reflux. Persistent esophagitis can cause erosions and ulcers and lead to scarring and narrowing and also irreversible injury to the esophagus.

In some patients, as the esophageal lining becomes increasingly damaged, the body may attempt to try to protect it by changing the lining material to a more resistant type, such as found in the intestine. This change, called Barrett's Esophageal Metaplasia, or Barrett's Esophagus, does not make the symptoms disappear but actually produces a new problem. Metaplastic changes increase the risk of a cancer forming in the new and abnormal lining. Adenocarcinoma of the Gastresophageal Cardia is a highly malignant and fatal type of cancer, the incidence of which is increasing rapidly in America. Some authorities believe that Barrett's esophagus is caused by bile reflux and that the rising incidence of this particular type of cancer is due to the increasing use of medication that suppresses acid production, thus allowing the alkaline bile to reflux unopposed into the esophagus.

The symptoms of acid reflux are uncomfortable, and some sort of relief is usually sought. Some patients chew antacid tablets, sleep on several pillows, or even sleep upright in a recliner. Those with frequent symptoms are treated with drugs that interfere with the formation of acid in the stomach such as Tagamet®, Zantac®, Pepcid®, and Prilosec®. These medications work well in relieving symptoms, till the next dose is due, but they have to be taken daily, often for life, and the cost is substantial (around $1,300 per patient per year).

Moreover, these medications relieve the symptoms, but do not correct the underlying problem.

Currently, the only way to restore the valve function is to operate under a general anesthetic. In the past, the operation was a complex undertaking, entailing a large abdominal or thoracic incision, a lengthy stay in hospital, and a prolonged absence from work. Today, the operation can be done laparoscopically. This shortens the hospital stay, from about ten days to two or three days, but is still carried on under a general anesthetic, and is associated with a significant complication rate. Therefore gastroenterologists are often reluctant to refer patients to surgeons for anti-reflux surgery and many patients who should be operated upon are not.

It is estimated that in the USA alone, 65 million people suffer from heartburn and GERD symptoms are currently the most common complaint of patients who consult with gastroenterologists. According to the New England Journal of Medicine, nearly 40% of adult Americans suffer from heartburn; of those who seek treatment for symptoms of reflux esophagitis, 10 to 20% have serious complications (about 4-8% of the total adult population).

Surgical procedures are usually effective in controlling severe gastroesophageal reflux disease. Surgical procedures are designed to correct gastroesophageal reflux by creating a new functional lower esophageal sphincter and to repair a hiatal hernia when present. The most popular approach is the Nissen fundoplication or a modification of this technique [*The Esophagus,* 3rd Ed., Donald O. Castell, Ed., pp. 515-517]. It involves mobilization and wrapping of the fundus of the stomach around the lower esophagus. As pressure increases in the stomach it compresses the lower esophagus, preventing reflux. The procedure is performed after first placing a large dilator in the esophagus in order to prevent making the wrap too tight. Fundoplication performed by either a traditional open or laparoscopic technique should be identical, except that access to the esophagus by laparoscopy is through a series of four or five punctures in the abdominal wall, rather than by an upper abdominal incision. The advantages of the open technique include the ability to see structures in three dimensions and to palpate them. Laparoscopy provides a clear magnified view of the area of surgery and is associated with less pain and more rapid recovery postoperatively.

The procedure is illustrated in FIG. 1. The length of the suture "S" is 2.5 to 3.0 cm, and 2 to 5 sutures are typically required. Because wrapping the stomach "ST" 360 degrees around the esophagus "E", as shown in FIG. 1, is associated with inability or difficulty in belching and vomiting, partial fundoplications have been devised. These include the Toupet posterior partial fundoplication (270 degrees) [*Ibid,* pp. 517-518] illustrated in FIG. 2, in which "E" is the esophagus, "AW" is the anterior wall of wrap sutured to the esophagus, and "GJ" is the gastroesophageal junction, and the Thal anterior fundoplication (180 degrees), illustrated in FIG. 3, where "F" indicates the fundus being plicated.

All these procedures have an excellent track record in terms of safety, and ability to control both biliary and acid reflux. However, they can only be carried out laparoscopically or via a laparotomy (abdominal incision) or a thoracotomy (opening the chest). Either way, general anesthesia is required. Because of this disadvantage, the art has attempted do devise minimally invasive methods and apparatus that can be used to carry out fundoplication procedures. U.S. Pat. No. 5,403,326 describes a fundoplication method of the stomach to the esophagus that requires the introduction of an esophageal manipulator and a stapler into the stomach lumen, and the stapling the intussusception esophagus to the stomach. U.S. Pat. No. 5,558,665, and its related patent U.S. Pat. No. 5,787,897, disclose a variform intraluminal member that can be used to manipulate the fundus to a position where it can be fastened by other devices, and a method for carrying out such surgery. U.S. Pat. No. 5,571,116, and its related U.S. Pat. Nos. 5,676,674 and 5,897,562 describe a multi-stapler device, and associated staplers, for carrying out an automatic approximation of the lower esophagus and fundus of the stomach and for invaginating the gastroesophageal junction into the stomach, thereby involuting the surrounding fundic wall.

WO 00/53102 describes a method and apparatus for minimally-invasive fundoplication which requires using a gripping head to grip the fundus and to move it toward the esophagus. The device of this reference has the severe drawback of being unable to position the stapling head precisely, and therefore any attempt to carry out a fundoplication may result in dangerous damage being inflicted on the patient. Furthermore, it entails an undesirable perforation of the fundus by the gripping head.

Not with standing the great efforts made in the art to overcome the need for major surgery in the treatment of GERD, none of the abovementioned devices and methods have gained any actual popularity, and they are currently not in use. The reasons for this fact are many, and include the difficulty in controlling the operation of the device, the inherent disadvantages of the types of fundoplications that can be achieved by them, the ongoing need for additional invasive operations, particularly the laparoscopic introduction of devices, etc. It is therefore clear that there is a need in the art for a fundoplication method that can be effectively used for the treatment of GERD, and which is free from the above disadvantages of prior art methods and devices.

An endoscopic apparatus and method of using it, for the treatment of GERD, which overcomes many of the aforementioned drawbacks of the prior art has been described in published International Patent Applications WO01/67964, WO/02/39909, WO02/24058, WO02/068988, WO2005/002210, WO2005/115221, WO2005/115255, WO2005/120329, and WO2006/033109 by the same applicant hereof, the descriptions of which, including publications referenced therein, are incorporated herein by reference.

It is therefore a purpose of the present invention to provide a transgastric method for the endoscopic partial fundoplication for the treatment of GERD that is simpler, safer, quicker and more effective than the methods of the prior art.

It is another purpose of the present invention to provide an endoscopic system for carrying out a transgastric method for the endoscopic partial fundoplication for the treatment of GERD.

Further purposes and advantages of this invention will appear as the description proceeds.

SUMMARY OF THE INVENTION

The invention is a transgastric method for the endoscopic partial fundoplication for the treatment of gastroesophageal reflux disease (GERD). The method comprises the steps:
(a) introducing the endoscope through the mouth and esophagus into the stomach of the patient;
(b) cutting a hole in the wall of the stomach;
(c) pushing the endoscope through the hole;
(d) grabbing the tissue at a location on the outer surface of the stomach and moving the grabbed tissue closer to the esophagus;
(e) positioning the staple cartridge in the esophagus;
(f) making final adjustments prior to firing the staples;
(g) firing the staples;
(h) releasing the endoscope from its firing configuration;
(i) removing the endoscope from the body of the patient; and
(j) closing the hole.

In one embodiment of the method the endoscope is rotated one or more times after step (h) and after each rotation steps (d) to (h) are repeated at a different location. In a preferred embodiment the endoscope is rotated two times, by 90 to 100 degrees each time, and the different locations at which the tissue is grabbed are: the exterior of the fundus, the exterior of the anterior wall, and the exterior wall of the stomach on or near the lesser curvature.

In preferred embodiments of the method of the invention the hole is made in the upper anterior wall of the stomach near to the greater curvature of the stomach.

In a preferred embodiment of the method of the invention step (a) comprises:
(a) activating the visualization means located on the endoscope to be able to observe the stages of the procedure;
(b) introducing the endoscope in its straightened configuration through the mouth and the esophagus of the patient into the stomach;
(c) partially bending the articulation section after the distal end of the endoscope enters the interior of the stomach; and
(d) guiding the distal face to a location close to the anterior wall near the greater curvature of the stomach.

In a preferred embodiment of the method of the invention step (b) comprises the steps of: cutting a hole in the anterior wall by means of a surgical cutting device that is guided to the site through the working channel of the endoscope and withdrawing the cutting device from the working channel after the hole is made; step (c) comprises: pushing the distal tip of the endoscope through the hole to the outside of the stomach and further advancing the endoscope distally and bending the articulation section until the distal tip is close to the outer wall of the stomach; step (d) comprises: grabbing the tissue on the outer wall of the stomach with a grabbing tool that is passed through the working channel and exits the distal face of the endoscope and further bending and moving the articulation section until the grabbed tissue is pulled close to the outer wall of the esophagus; and step (e) comprises: moving the curved endoscope as necessary until the stapler cartridge is located in the esophagus a distance about three centimeters above the LES and rotated until the stapler cartridge faces the direction of the greater curvature of the stomach and locking the endoscope in position. The endoscope can be locked in position by means of locking screws provided in a bite block located in the patient's mouth.

In a preferred embodiment of the method of the invention step (f) comprises:
(a) activating the ultrasound positioning system to aid in final alignment of the anvil unit with the cartridge;
(b) advancing the locking screws out of the anvil unit and into the bores in the staple cartridge;
(c) halting the action of the mechanism that advances the screws when the signals from the ultrasound system indicate that the proper distance between the faces of the anvil and the staple cartridge has been achieved;

(d) releasing the hold of the grabbing tool on the tissue of the stomach and retracting the grabbing tool into the working channel; and (e) making a final visual and ultrasonic confirmation that the endoscope is in the proper position and that the anvil and the cartridge are in the correct working relationship.

In a preferred embodiment of the method of the invention step (h) comprises:

(a) loosening the locking screws and visually inspecting the area to verify that the legs of the staples have properly curled and that the tissue is fastened correctly;

(b) totally withdrawing the screws into the anvil unit;

(c) partially unbending the articulation section; and (d) unlocking the endoscope The hole can be closed by means of one or more of the following: sutures, staples, clips, or. In a preferred embodiment staples are applied by means of a dedicated endoscopic stapling device especially designed for the task of closing holes in tissue. Embodiments of the dedicated endoscopic stapling device can be discarded after a single use. The surgical cutting device can be a RF cutter, a laser, an ultrasonic cutter or an endoscopic scalpel. The grabbing tool can be a forceps or a screw comprised of stiff wire bent into a spiral shape.

All the above and other characteristics and advantages of the invention will be further understood through the following illustrative and non-limitative description of preferred embodiments thereof, with reference to the appended drawings.

BRIEF DESCRIPTION OF THE DRAWINGS

FIGS. 20A to 20F schematically show different stages in the operation of the front fastening embodiment of the endoscopic stapler used to close a hole in biological tissue.

DETAILED DESCRIPTION OF PREFERRED EMBODIMENTS

The present invention employs the various embodiments of endoscopic apparatus described in the above referenced published International Patent Applications WO01/67964, WO/02/39909, WO02/24058, WO02/068988, WO2005/002210, WO2005/115221, WO2005/115255, WO2005/120329, and WO2006/033109. In WO01/67964, which is the initial publication in this series, is described an endoscopic device with a surgical stapler attached to its shaft in such a way that bending the articulation section of the endoscope through an angle of 270° brings the anvil of the stapler, located on the distal tip of the endoscope, into correct working position with the cartridge containing the staples and staple firing mechanism, located on the proximal end of the articulation section. The endoscope-stapler unit is especially suited for performing fundoplication procedures as a treatment for GERD. Experienced persons will realize however, that the basic device itself and in particular the improvements to many of its components and subsystems described in the other above referenced applications are not limited to any particular application and can be either used as described or modified mutatis mutandis by skilled persons for many applications in medicine and industry.

Figure 4A:
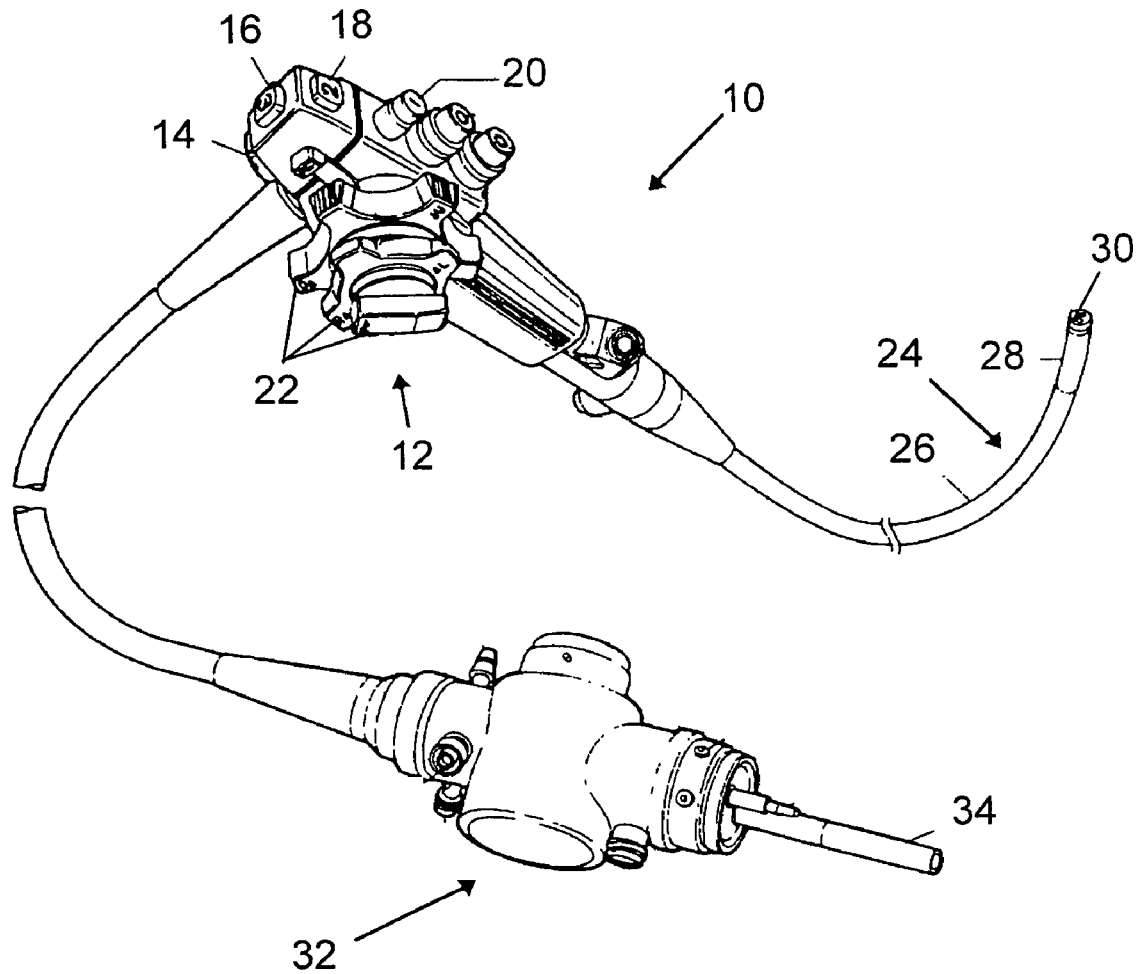
FIGS. 4A and 4B schematically illustrate a conventional endoscope.
Figure 4B:
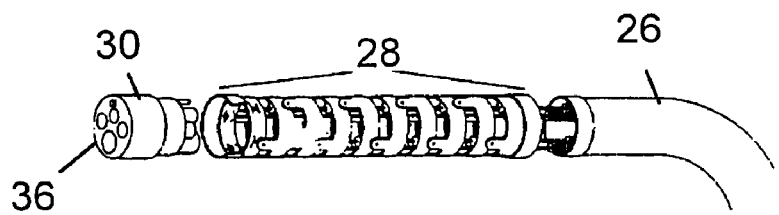

A conventional endoscope is illustrated in FIGS. 4A and 4B. Briefly the endoscope illustrated in FIG. 4A and generally indicated at 10, is provided with a control section 12 (referred to as the "handle", "control handle", "operating handle") provided with suction valves, operating switches, angulation lock, etc., switches 14-20 being marked for illustrative purposes. Control wheels 22 are used for implementing the bending of the articulation section, locking the articulation section, activating accessories such as a stapler, etc. The endoscope 10 also comprises a connector section 32, used to connect air and water inlets, light guides, etc., the light guide being indicated at 34, for illustration purposes. The insertion tube 24 consists of three separate sections: a flexible portion 26, an articulation section 28 and a distal tip section 30. These latter three sections are shown in greater detail in FIG. 4B, in which is also shown the distal end 36.

The handle of the endoscope includes connections, control knobs, and mechanisms for carrying out the functions of the endoscope. These functions include conventional operations, e.g. articulation, staple firing, and specialized operations, e.g. staple cartridge indexing, advancement of the screws that lock the anvil to the cartridge, ultrasonic positioning that are unique to the endoscopes described in the above referenced patent applications, which are suitable for carrying out the procedure of the present invention. The handle is connected by means of the universal multi-connector, vacuum and water lines, etc. to an endoscopy suite such as that described in WO2005/120329.

Figure 10:
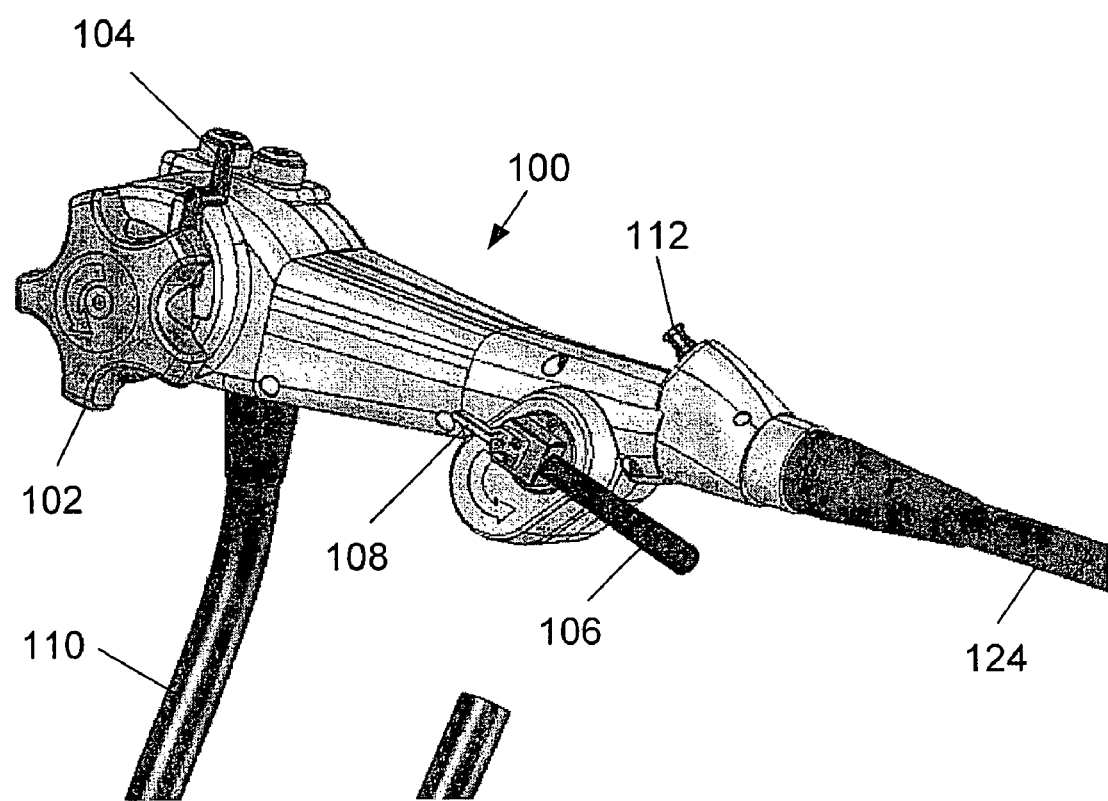
FIG. 10 shows the handle of the endoscope used to perform the transgastric partial fundoplication.

In FIG. 10 is shown an illustrative handle 100 that comprises all of the control elements needed to perform the method of the invention described herein. In this figure are seen: the control knob 102 for bending of the articulation section with associated lever 104 which activates a ratchet mechanism for fine control of the bending and also locking the articulation section; the staple firing lever 106 and associated locking lever 108, which prevents accidental firing of the staples; the entrance port to the working channel 112; the proximal end of the insertion tube 124; and the cable to the endoscopy suite 110. Not seen in FIG. 10 is the control lever for indexing the cartridge after each array of staples is fired, whish is located on the back side of the handle opposite the staple firing levers.

Figure 5A:
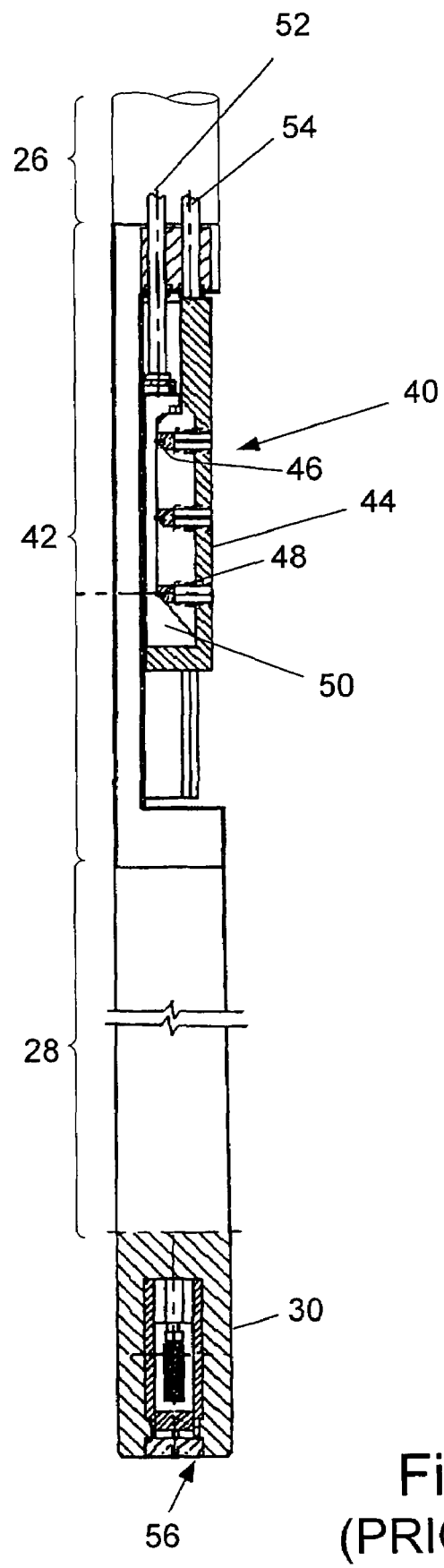
FIG. 5A schematically illustrates the fixed portion and the articulation distal portion of an endoscope, comprising a stapler according to the prior art.

In FIG. 5A is shown the distal portion of the insertion tube of an endoscope that is suited for carrying out the GERD procedure of the invention. The endoscope described herein is first disclosed in WO01/67964. The insertion tube in this endoscope comprises a staple deployment system located in a recess 40 in a rigid section 42 that is positioned between articulation section 28 and distal tip section 30. The staple deployment system comprises a staple storage facility (cartridge 40) and staple firing mechanism. The stapler deployment system has a side firing design and requires an anvil which is located on distal end 36 of the endoscope. The anvil is part of an anvil module 56 located in a recess in the distal tip 30. Both the stapler cartridge 40 and the anvil module 56 are preferably replaceable.

The staple and storage firing mechanism comprises staple cartridge 44 containing one or more (three are shown) arrays of staples 46. The staples are fired by pulling firing cable 52 and the attached cams 50 (located in the cartridge) proximally thus forcing staple pushers 48 to move side wards and pushing the staples out of the cartridge 44. Numeral 54 designates the indexing mechanism used to ready the next array of staples for firing by moving them into position opposite the anvil.

The articulation section 28 is similar in design to that of conventional endoscopes, but possesses several unique features. Firstly, in order to simplify the alignment procedure and at the same time achieve maximum accuracy, a two-way articulation design is preferred. This generally means that the articulating section is constrained to bend in one plane only. Secondly, the device is able to bend up to 270° in order to carry out the required medical procedure, which is further than in conventional endoscopes. Finally, the articulating section is strong enough to provide a significant force against the tissues during fundus distension, clamping, and stapling (as described in WO 01/67964, with reference to the illustrative surgical procedure).

Figure 5B:
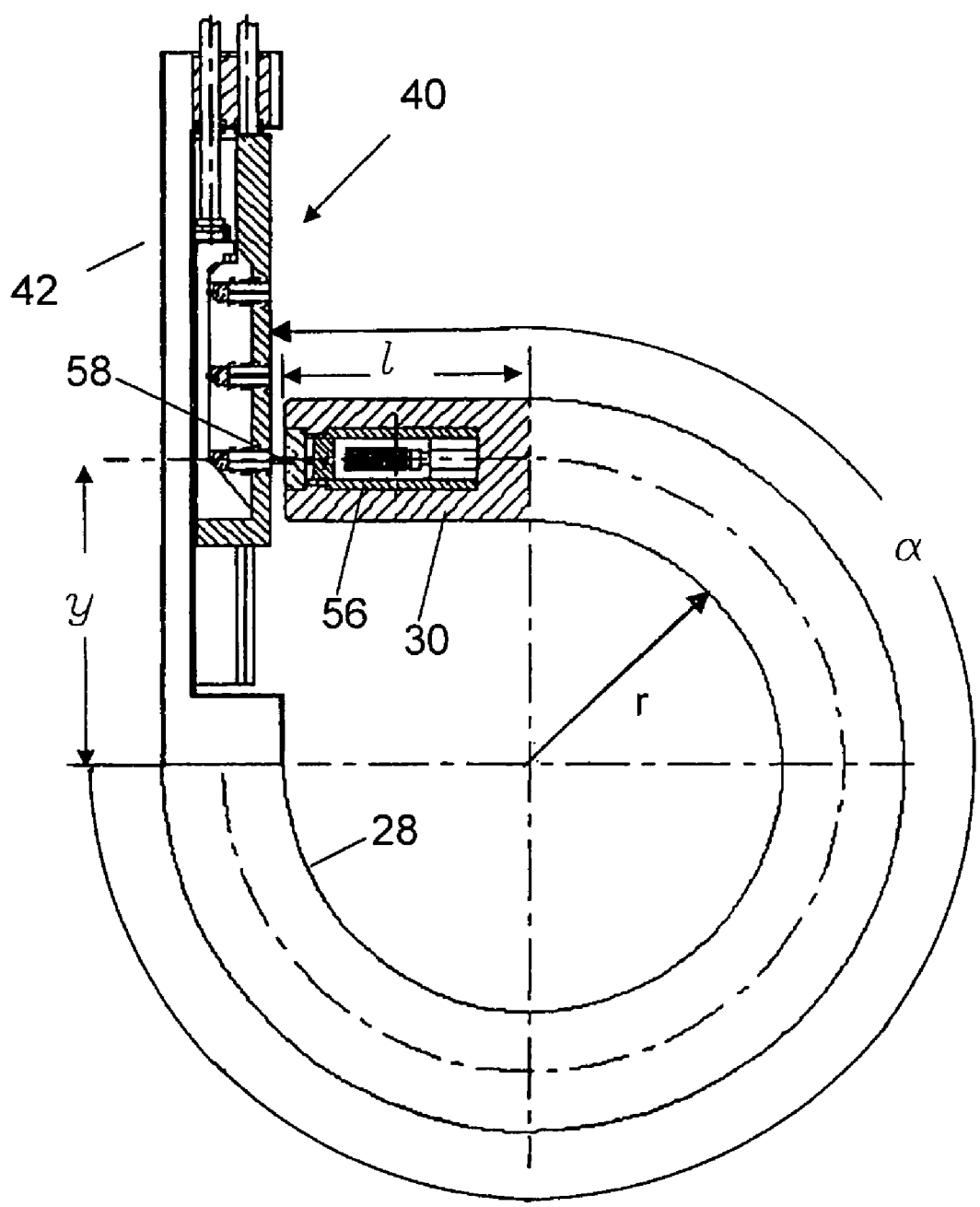
FIG. 5B schematically illustrates the articulation of the endoscope of FIG. 5A through its maximum bending angle.

FIG. 5B schematically shows the device of FIG. 5A in a fully articulated position. The articulation section 28 has been bent through bending angle α using fixed radius of curvature "r". The values of radius "r" and the length of the articulation section are determined by the fixed values "l" (length of the distal tip section 30) and "y" (the distance from the position at which the stapling is to be carried out to the interface of the rigid section 42 and the articulation section 28 of the endoscope) in such a way that articulation of the device completely brings the two parts of the stapler assembly essentially into alignment. Final alignment is aided by various means (not shown in any of the figures) such as an ultrasound system (best described in WO02/068988) and a special configuration of the matching faces of the anvil unit 56 and cartridge 44 (best described in WO2005/115255). When the anvil has been brought into correct working relationship opposite the cartridge screws 58 that are stored in anvil unit 56 are advanced into matching bores in the cartridge to provide exact alignment and distance and to clamp the two parts of the stapler together so that sufficient force can be applied when firing the staples to insure that the legs of the staples enter the recesses on the anvil and curl properly.

Figure 6:
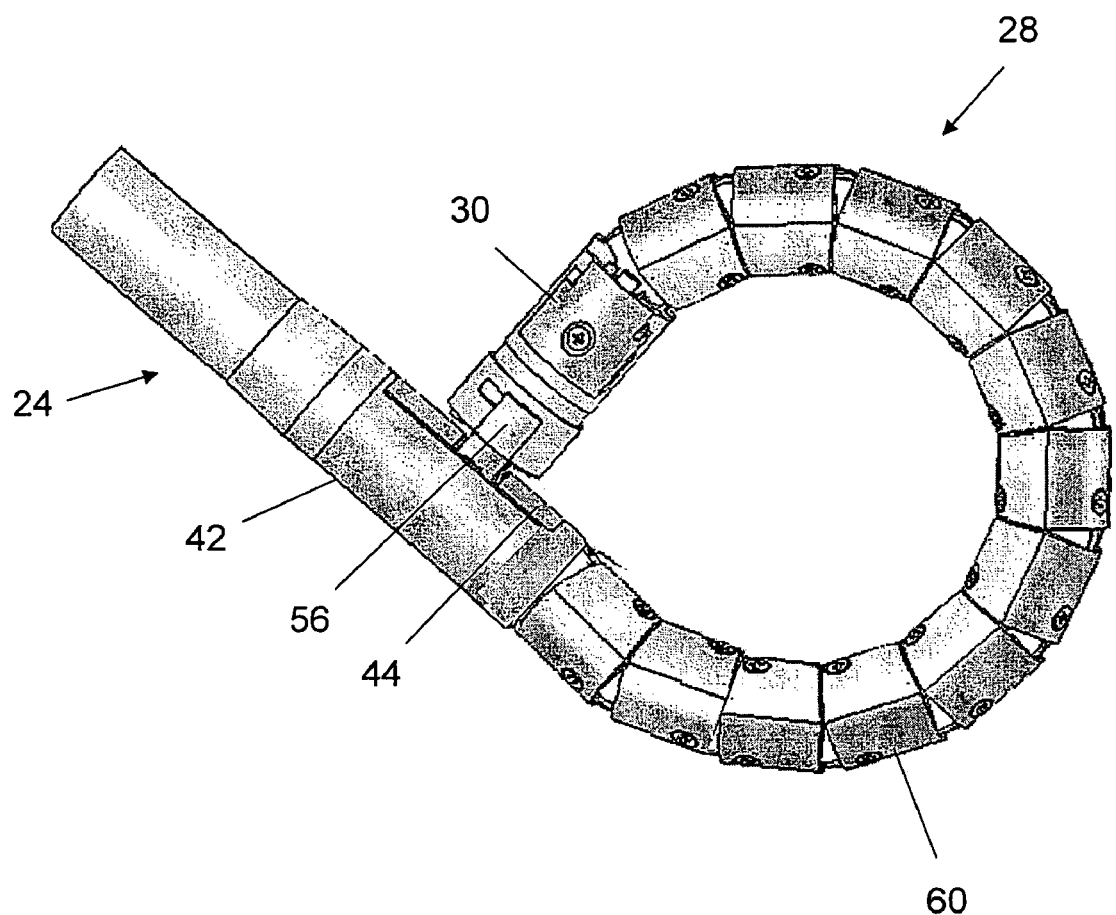
FIG. 6 shows a preferred embodiment of the articulation section of the GERD endoscope in its fully bent configuration.

In FIG. 6 is shown the preferred embodiment (described in WO2006/033109) of the articulation section 50 of the GERD endoscope in its fully bent configuration. In the embodiment shown, articulation section 28 comprises 10 identical vertebrae 52 and two more vertebrae at each end that are linked together end-to-end in a chain-like fashion. The two end vertebrae are nearly identical to the others except that the distal end of one and the proximal end of the other one are adapted to connect to distal tip 30 and rigid section 42 of the insertion tube 24 of the endoscope respectively.

The articulation section of the GERD endoscope is designed to provide two-way articulation through an angle of about 270 degrees. That is, as shown in FIG. 6, the articulation section can be bent in one direction in a plane that contains the longitudinal axis of the endoscope until the distal tip is brought to a position opposite the rigid section in the shaft of the endoscope. When in this position the anvil unit 56 and the cartridge 44 are said to be in correct working relationship.

Figure 7:
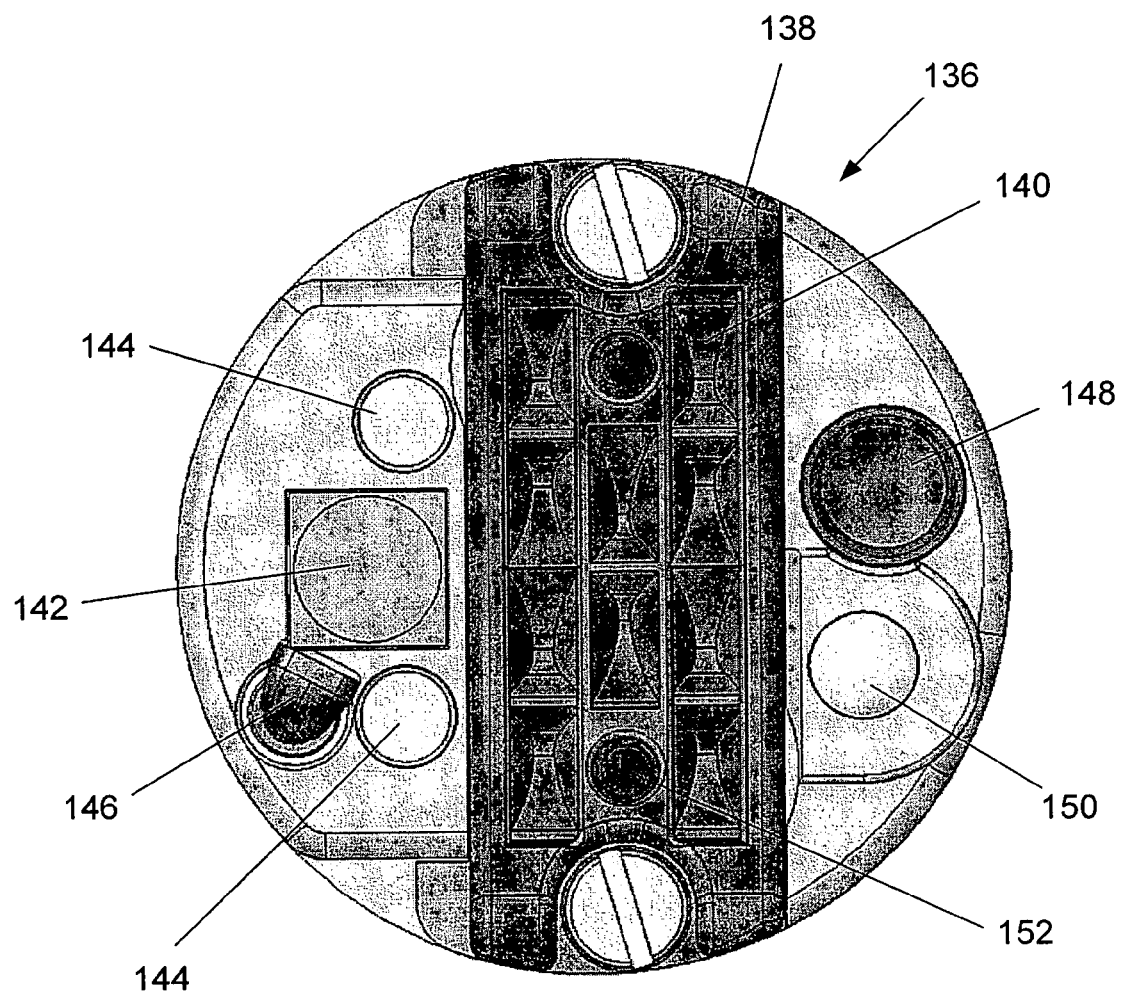
FIG. 7 schematically shows the distal face of the GERD endoscope.

FIG. 7 schematically shows the distal face 136 of the GERD endoscope used to perform the procedure of the invention. Shown in the figure is an imaging channel is 142. Numeral 144 represents illumination fibers and numeral 146 designates a nozzle for spraying water or air to clean the objective lens of the camera. The preferred imaging method is to place an electronic camera unit (described in detail in WO2005/002210 and WO2005/115221) at the distal end of channel 142. Placement of imaging means at the distal tip assists in guiding the device to the desired position in the body lumen and allows imaging of the area during the performance of the surgical procedure. The endoscope may contain two or more separate optical channels that produce two or more distinct views, e.g. a second optical imager can be provided to view through a clear portion of the stapler and will to show the staples as they are passed through the tissue and bent closed. Various embodiments of suitable endoscopic optical systems are described in WO02/24058.

Numeral 138 designates the anvil unit face; numeral 152 designates the alignment/locking screws, which are contained in the anvil unit; and numeral 140 designates the depressions for curling the legs of the staples when they are ejected from the cartridge. Numeral 150 designates an ultrasound transducer or reflector that is part of the alignment system. A working channel for introducing surgical tools, suction, or irrigation is shown at 148. The skilled person will understand that other options can be provided and other configurations are allowed depending on the requirements of the endoscopic procedure to be performed. For example, more than one working channel 70 can be provided.

Figure 8A:
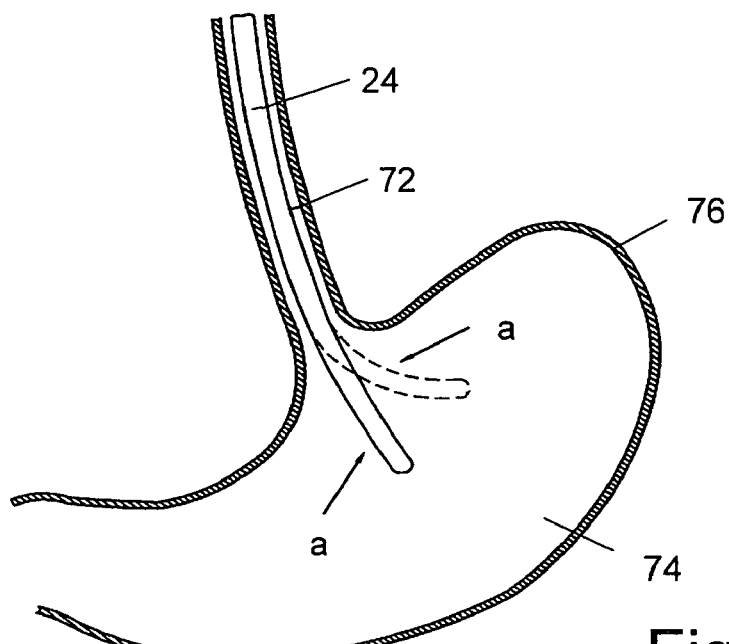
FIGS. 8A, 8B, and 8C schematically illustrate the mechanical procedure involved in the prior art endoscopic fundoplication procedure.

A prior art endoscopic procedure using the same endoscopic devices as the present invention to carry out a partial fundoplication is described in detail in WO01/67964. The procedure is carried out by bending the articulation section of the endoscope so as to engage the fundus of the stomach with the distal tip, and to move it toward the lower esophagus. This is schematically illustrated in FIG. 8 (A, B, and C). In FIG. 8A, two positions of the device are shown, "a" and "a'". Position "a" is the initial position after the insertion tube 24 has been inserted through esophagus 72 into the stomach 74. Position "a'" illustrates the beginning of bending of articulation section 28 (FIG. 5A) of the device, towards the fundus 72.

Figure 8B:
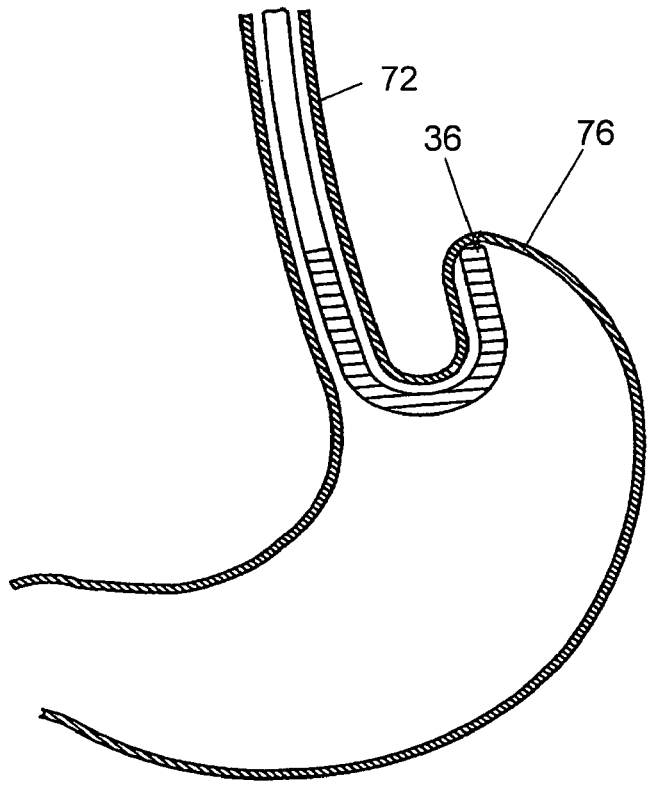

In FIG. 8B, the articulation of the device has proceeded to the stage in which the distal face 36 has encountered the wall of the fundus 76 and started to push it towards the lower region of the esophagus 72.

Figure 8C:
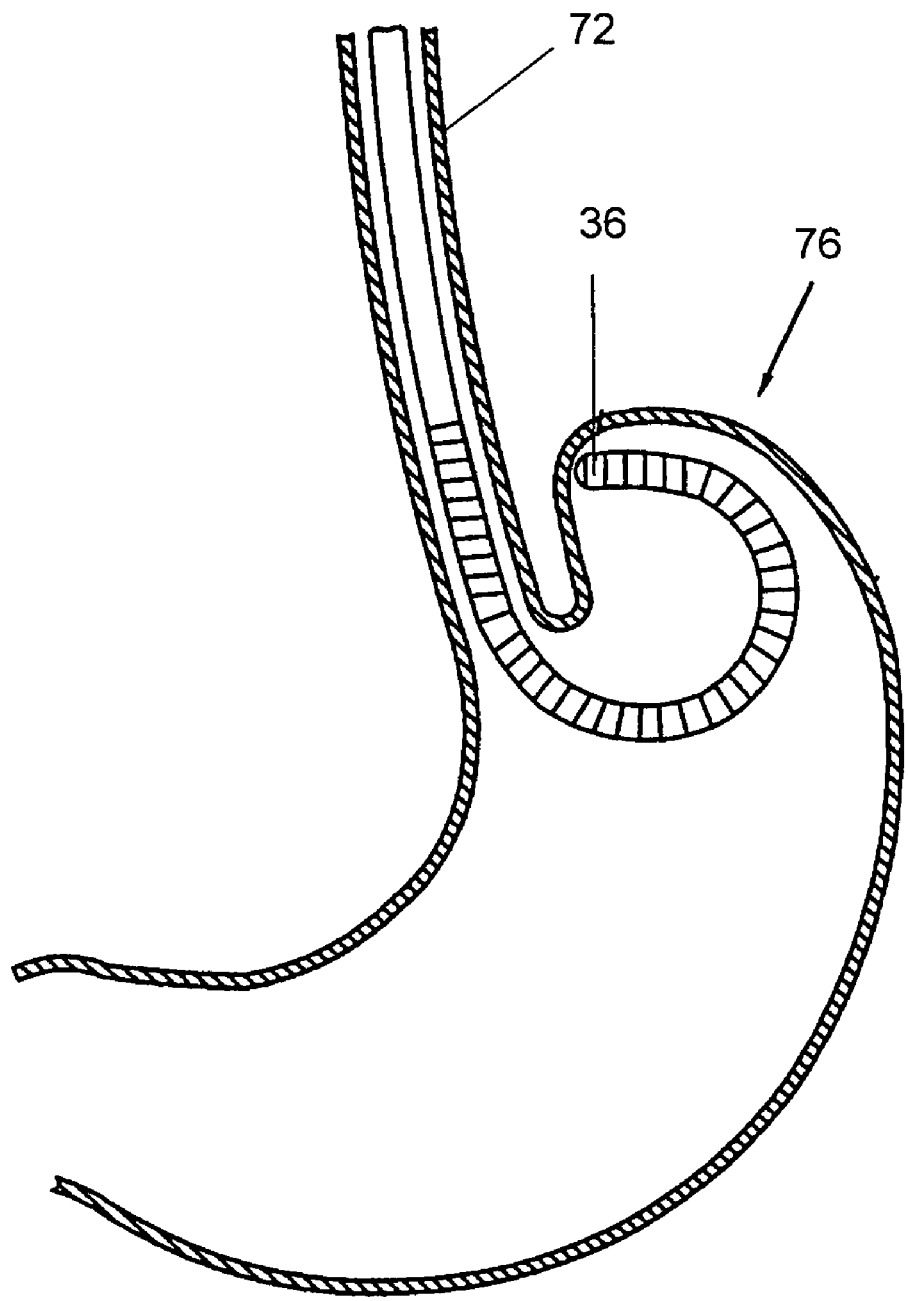

In FIG. 8C, the situation shown is that in which the articulation of the device has been almost completed, and the distal face 36 has pushed the wall of fundus 76 from its original position to a position near the lower esophagus 72. In this position, the fundus 76 is correctly positioned by distal face 36 and it is possible to carry out the stapling together of the tissue of the fundus 76 to that of the esophagus 72.

Figure 8D:
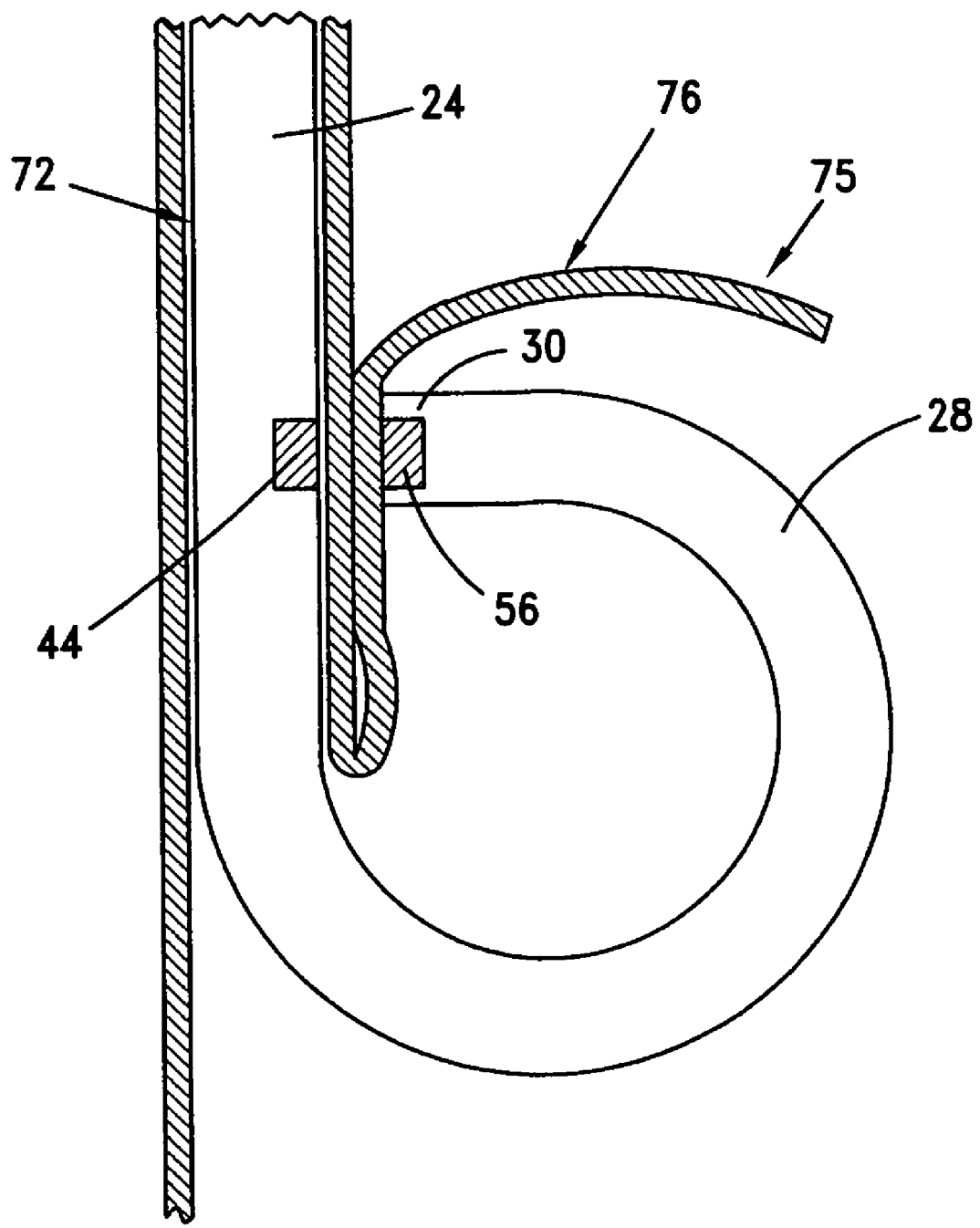
FIG. 8D schematically illustrates the positioning of the stapler prior to stapling the tissue of the fundus to the esophagus.

FIG. 8D is a more detailed view of the situation when the articulation of the endoscope has been completed. Here is schematically shown the alignment between the staple cartridge 44, mounted in distal end of the insertion tube 24 on the proximal side of the articulation section 28 of the endoscope within the esophagus 72, and the anvil 56 mounted on the distal tip 30 at the distal end of the articulation section 28 located within the stomach 74.

The transgastric procedure of the present invention is illustrated in FIGS. 9A to 9D. In these figures the anterior wall 80 of the stomach has been removed to enable easier visualization of the relative position of the endoscope during the various stages of the procedure.

The endoscope is introduced in its straightened configuration through the mouth of the patient (preferably through a bite block) and the esophagus 72 into the stomach 74. After the distal end of the endoscope enters the interior of the stomach, the articulation section 28 is slightly bent and the distal face 36 is guided to a location close to the anterior wall 80 near the greater curvature 78. This is the situation shown in FIG. 9A. At this point a hole is cut in the anterior wall 80 by means of a surgical tool, e.g. a RF cutter, energy from a laser, ultrasonic energy, or an endoscopic scalpel, that is guided to the site through working channel 70 in the endoscope.

Figure 9A:
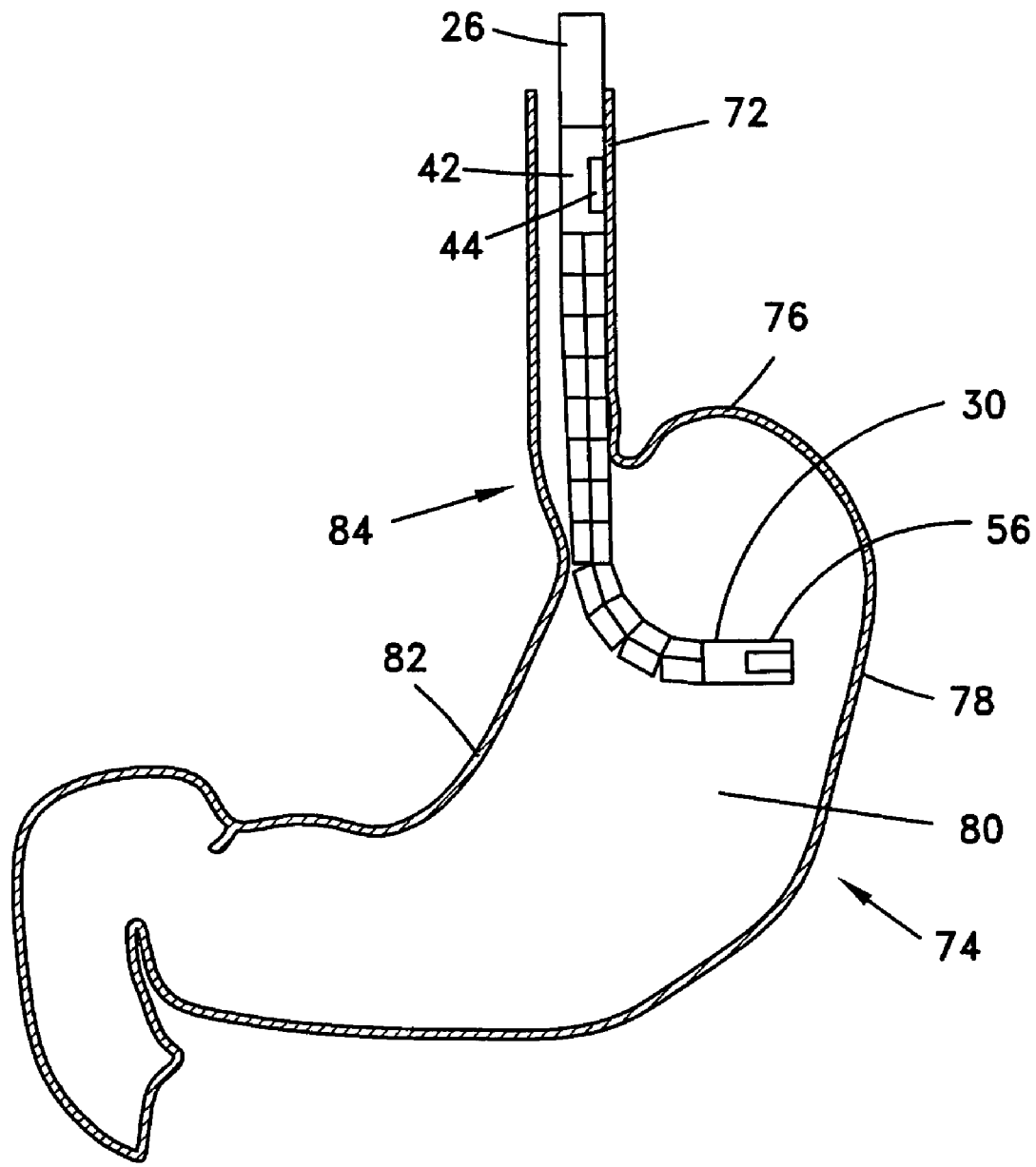
FIGS. 9A to 9D illustrate the transgastric procedure of the present invention.
Figure 9B:
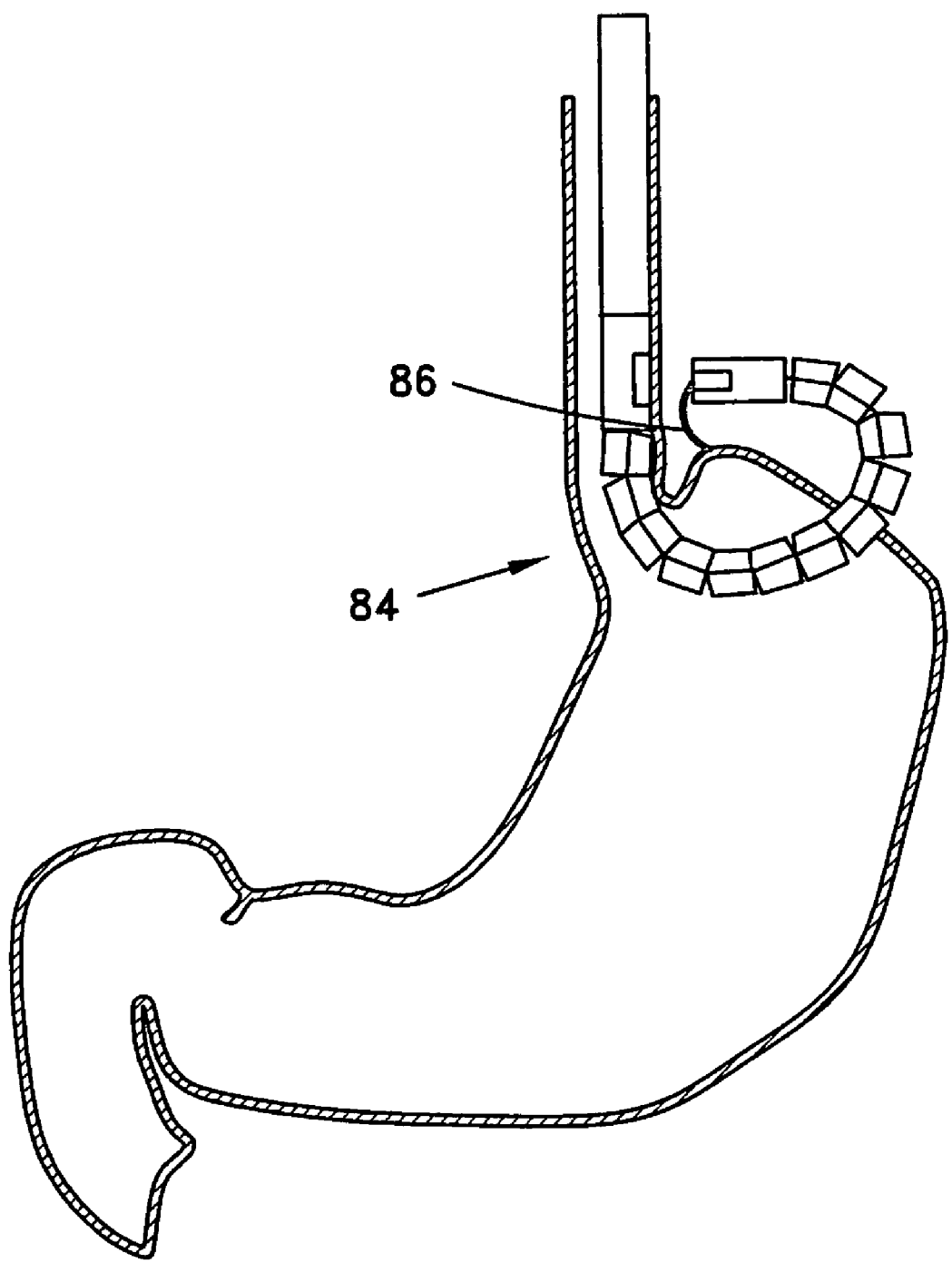

Once the hole is made, the cutting device is withdrawn from the working channel and the distal tip of the endoscope is pushed through the hole to the outside of the stomach. The endoscope is further advanced distally and the articulation section bent until the distal tip is close to the outer wall of the fundus 76. In this location, as shown in FIG. 9B, the tissue on the outer wall of the fundus 76 is grabbed by a gabbing tool 86, e.g. forceps or screw, which exits the distal face through working channel 70 to grab the tissue.

Figure 9C:
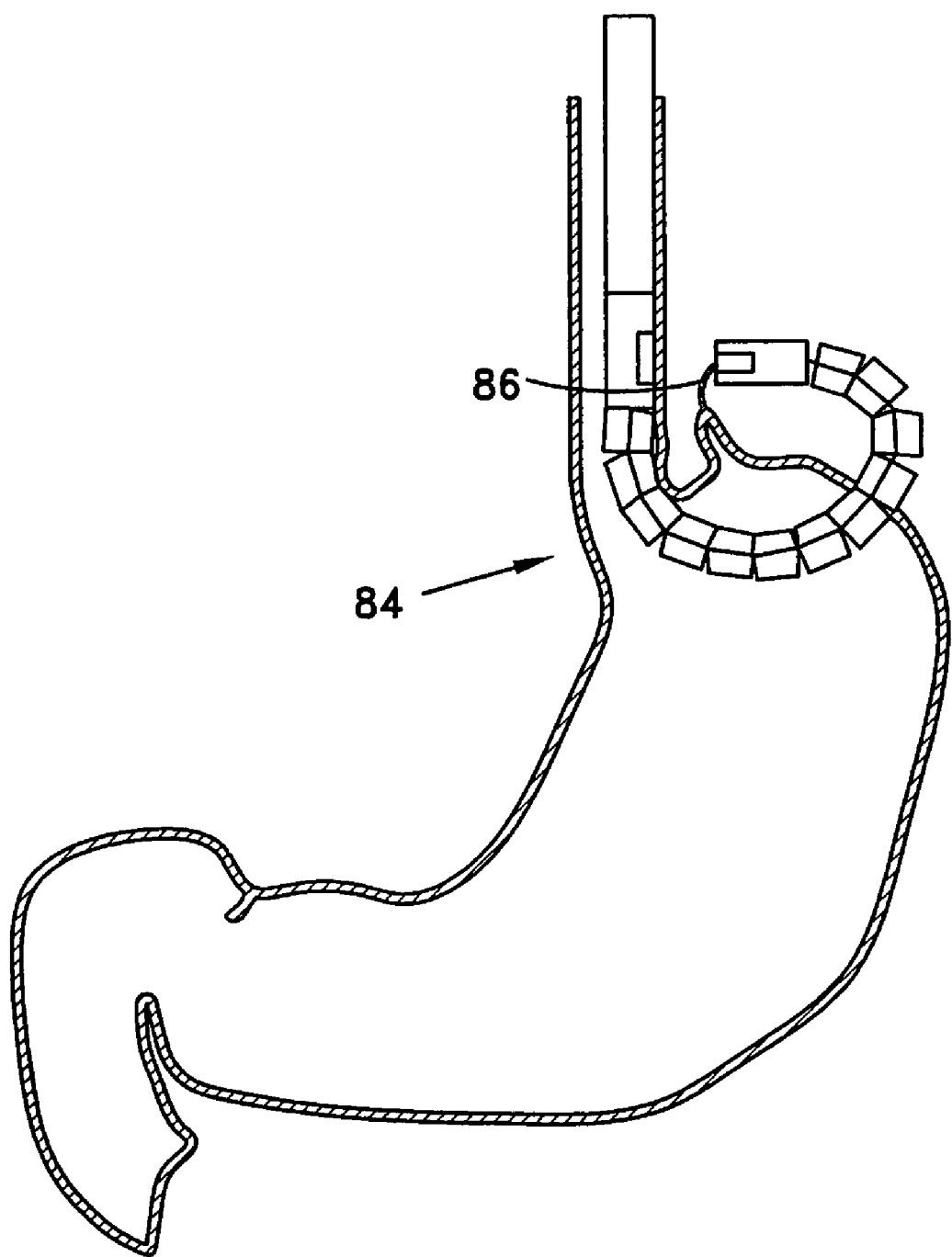

After the tissue has been grabbed, the articulation section is further bent and moved until the grabbed tissue of the fundus is pulled close to the outer wall of the esophagus as shown in FIG. 9C. At this point, the curved endoscope is moved as necessary until the stapler cartridge is located in the esophagus a distance about three centimeters above the LES 84 and rotated until it faces the direction of the greater curvature of the stomach 78. The endoscope is now locked in position by conventional means, e.g. locking screws provided in the bite block or in the handle of the endoscope.

Figure 9D:
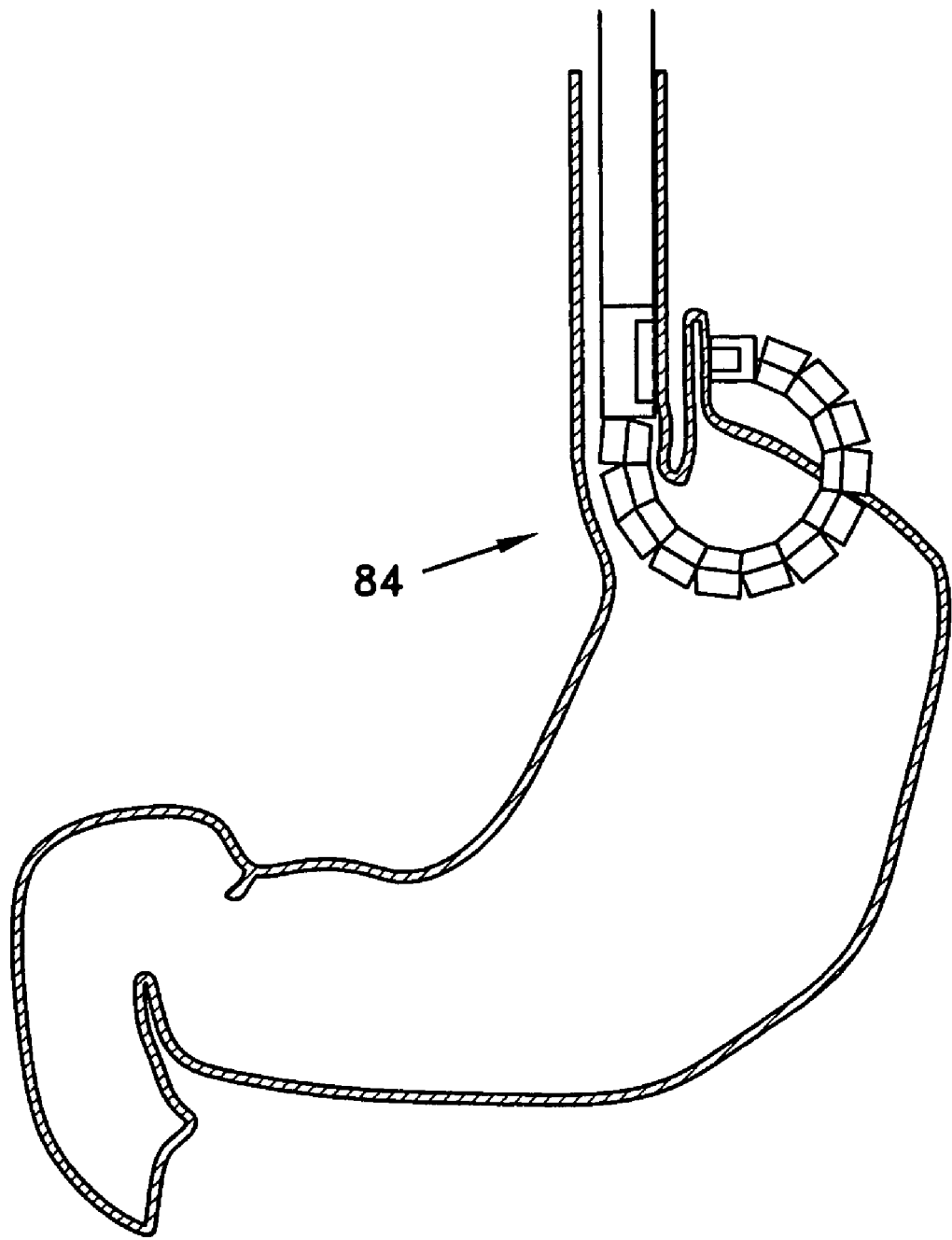

All the previous stages of the procedure and endoscope alignment are carried out under visualization using the visualization means located on the endoscope. When the articulation section has been bent very close to 270 degrees, the distal face gets very close to the outer wall of the esophagus, the tissue of the fundus is pressed between the distal face and the outer wall of the esophagus, and the anvil unit and cartridge are nearly in correct working position. At this point, which is shown in FIG. 9D, the ultrasound positioning system is activated to aid in final alignment. The locking screws 58 are advanced out of the anvil unit and enter the bores in the staple cartridge. As the screws enter the bores, the anvil is pulled closer to the cartridge compressing the layers of tissue between them. When the signals from the ultrasound system indicate that the proper distance between the faces of the anvil and the staple cartridge have been achieved, the action of mechanism that advances the screws is halted, the hold of the grabbing tool on the tissue of the fundus is released and the tool is withdrawn into the working channel. After a final visual and ultrasonic confirmation that the endoscope is in the proper position and that the anvil and cartridge are in the correct working relationship the firing cable is pulled and the array of staples is fired as described in, for example WO 01/67964.

After the staples are fired, the screws are loosened and the area visually inspected to verify that the legs of the staples have properly curled and that the tissue is held correctly. The screws are then totally withdrawn into the anvil unit, the articulation section partially unbent, and the endoscope released from the bite block and, in the preferred embodiments, partially pulled proximally to a position between that shown in FIGS. 9B and 9C.

Figure 1:
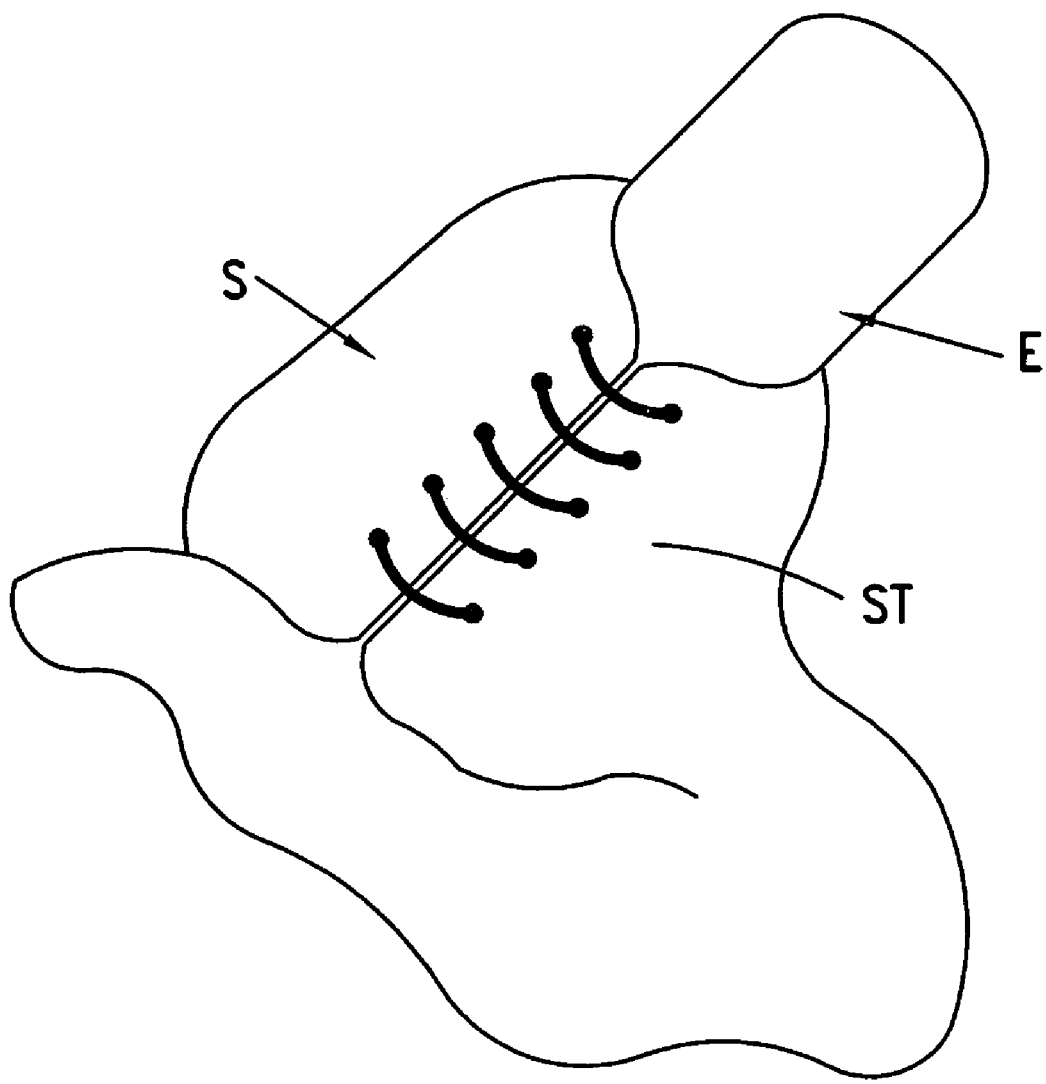
FIG. 1 illustrates the prior art wrapping of the stomach 360 degrees around the esophagus.
Figure 2:
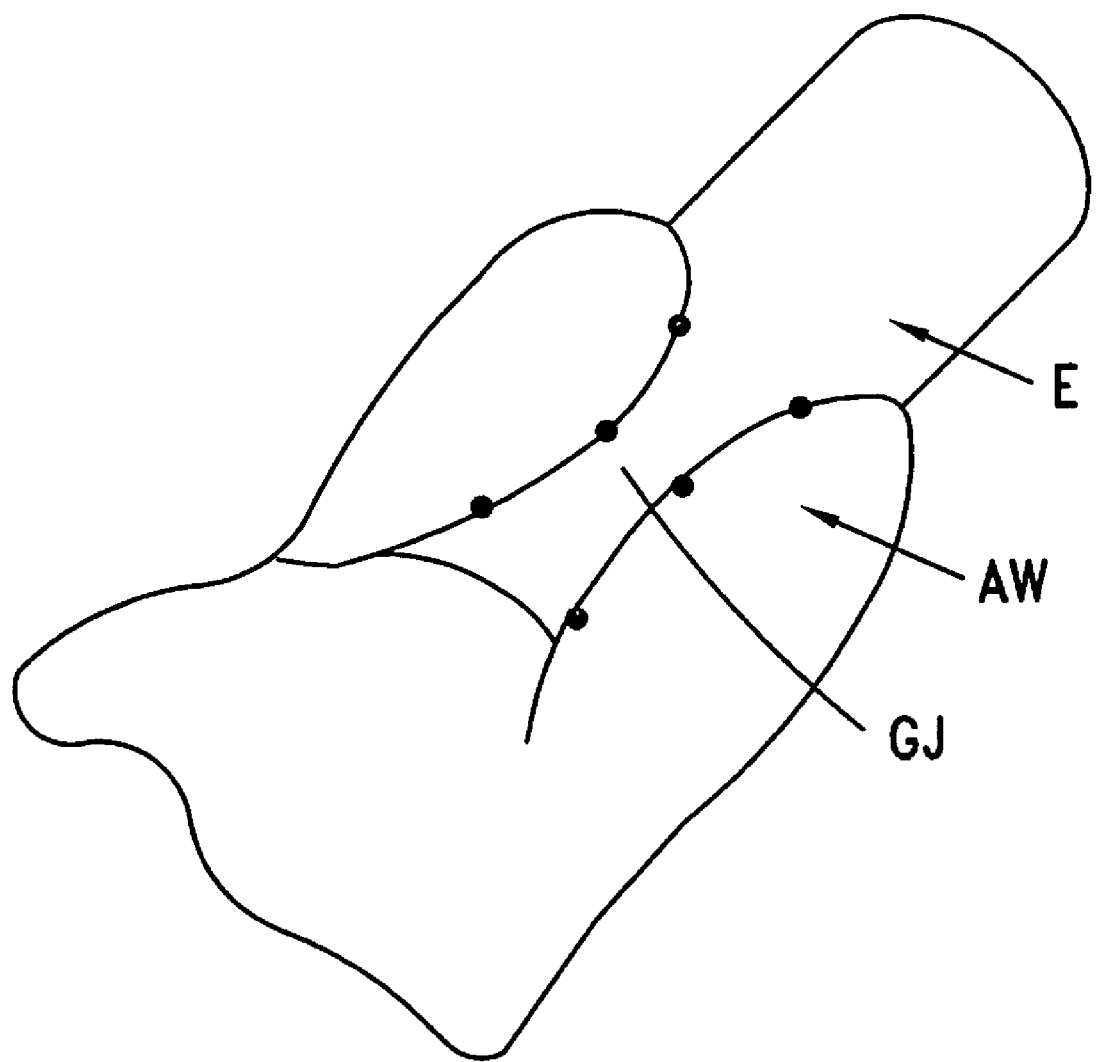
FIG. 2 illustrates the prior art Toupet posterior partial fundoplication (270 degrees)
Figure 3:
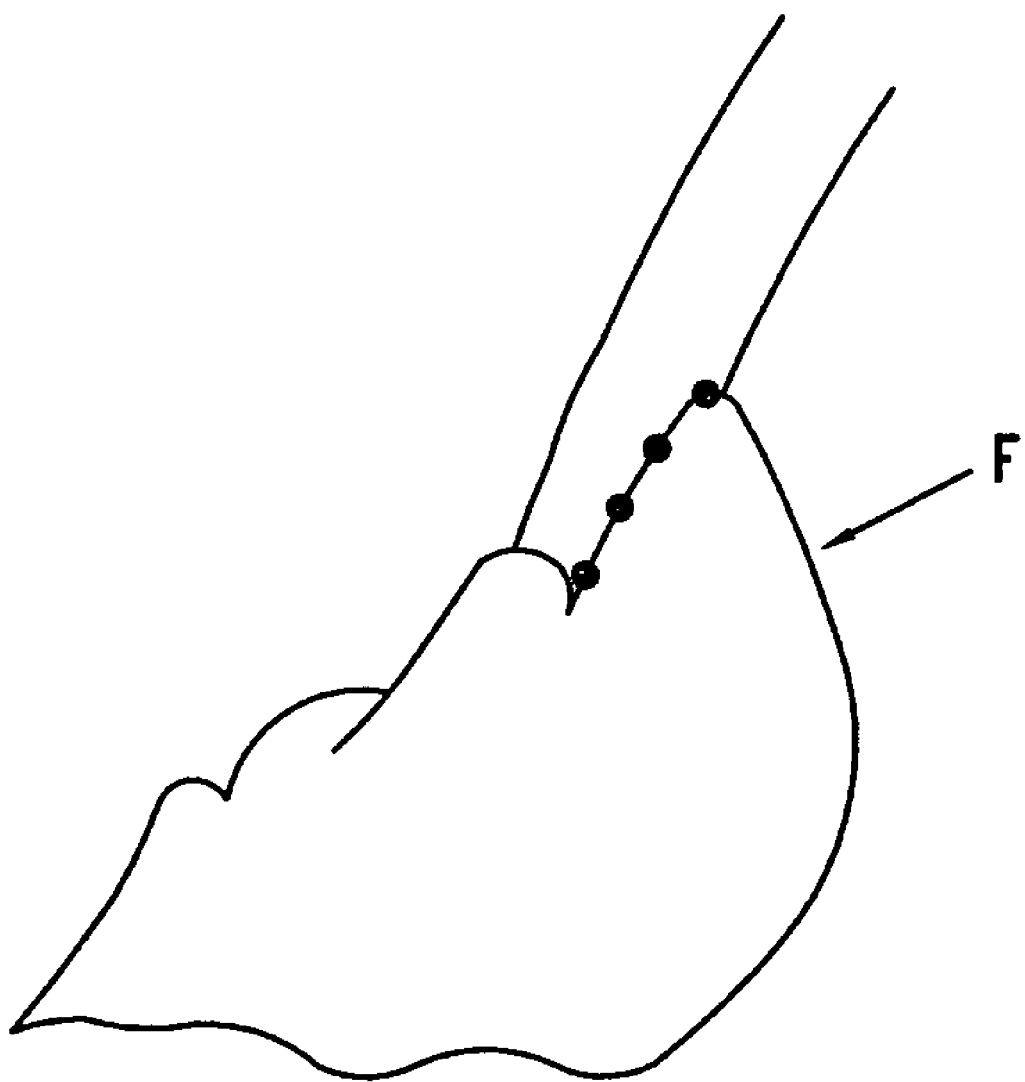
FIG. 3 illustrates the prior art Thal anterior fundoplication (180 degrees)

In the preferred embodiment of the partial fundoplication procedure, the tissue of the stomach is attached to the esophagus three times to create a Thal 180-200 degree anterior fundoplication as shown in FIG. 3. To create the partial fundoplication, the staple cartridge contains three arrays of staples and is indexed between the firing of each array, e.g. as described in WO01/67964.

After the first array of staples is fired and the anvil released from the cartridge, the endoscope is rotated 90-100 degrees around its vertical axis, the forceps is again extended from the distal face of the endoscope and used to grab the tissue on the outer surface of the upper part of the anterior wall of the stomach. The procedure is repeated a second time, thereby attaching the tissue of the stomach wall to the esophagus a second time. Finally the endoscope is rotated a further 90-100 degrees and tissue on the outside of the stomach from the area of the lesser curvature 82 is attached to the esophagus, thereby completing the partial fundoplication; whereupon the endoscope is straightened and withdrawn from the patient, after which the hole in the stomach wall is closed by means of sutures or staples or clip.

A preferred method of closing the hole is by means of a novel endoscopic stapling device that has been invented by the applicant of the present invention particularly for this purpose. The stapler device comprises an anvil and staple cartridge located in the distal tip of an endoscopic device which has an insertion tube that comprises a proximal flexible section followed by an articulation section. The stapler device has two embodiments, a side fastening embodiment and a front fastening embodiment in preferred embodiments is disposed after a single procedure is performed.

Figure 17:
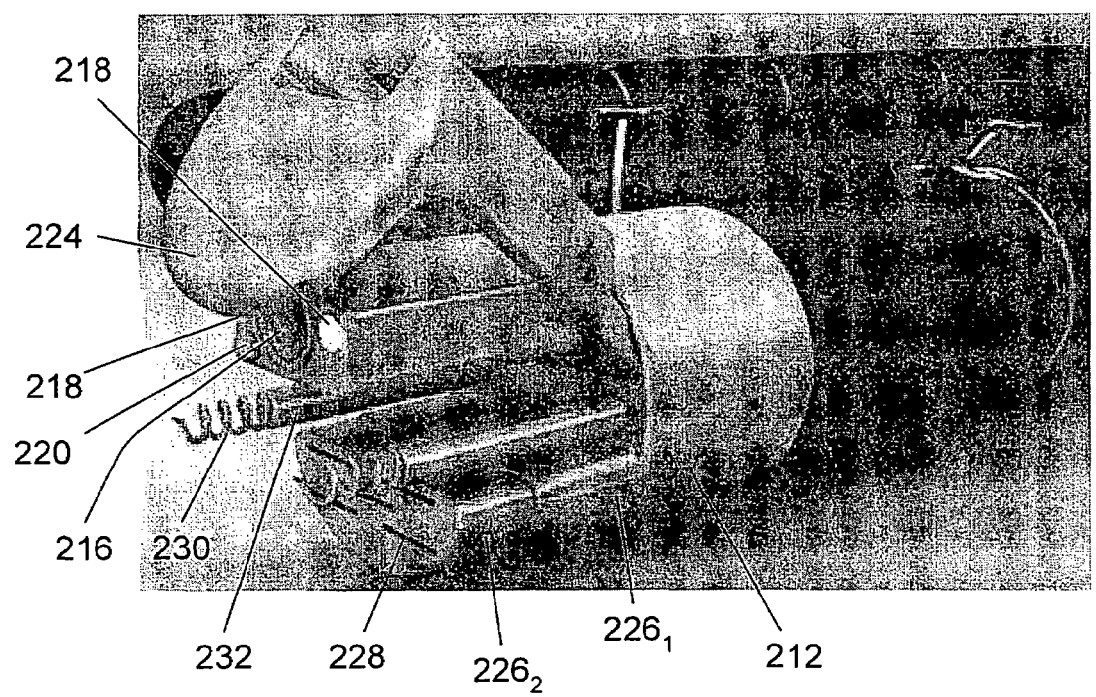
FIG. 17 to FIG. 19 show the front fastening embodiment of the stapler of the invention in the open and closed configurations respectively.
Figure 18:
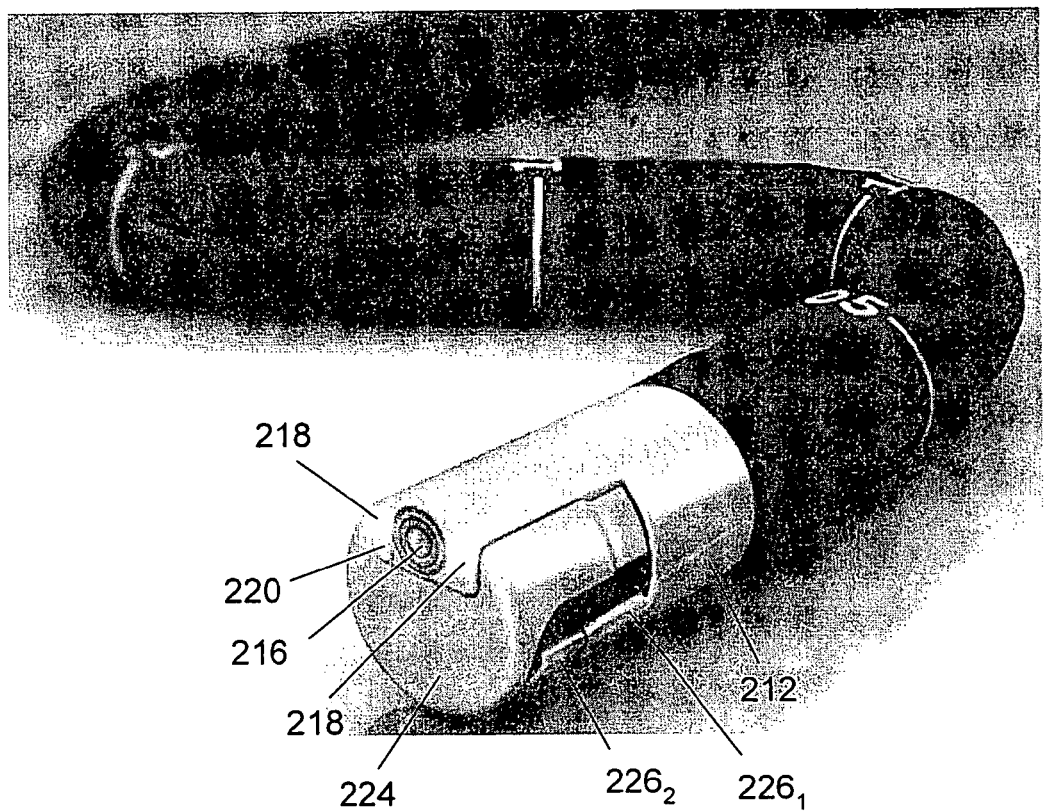

FIG. 11 to FIG. 15 show different views of the side fastening embodiment of the invention in order to assist in the description of the essential features of the stapler and its operation. FIGS. 16A to 16F schematically show different stages of the procedure of using the stapler device of the invention to close a hole in biological tissue. FIG. 17 and FIG. 18 show the front fastening embodiment of the stapler of the invention in the open and closed configurations respectively.

Figure 11:
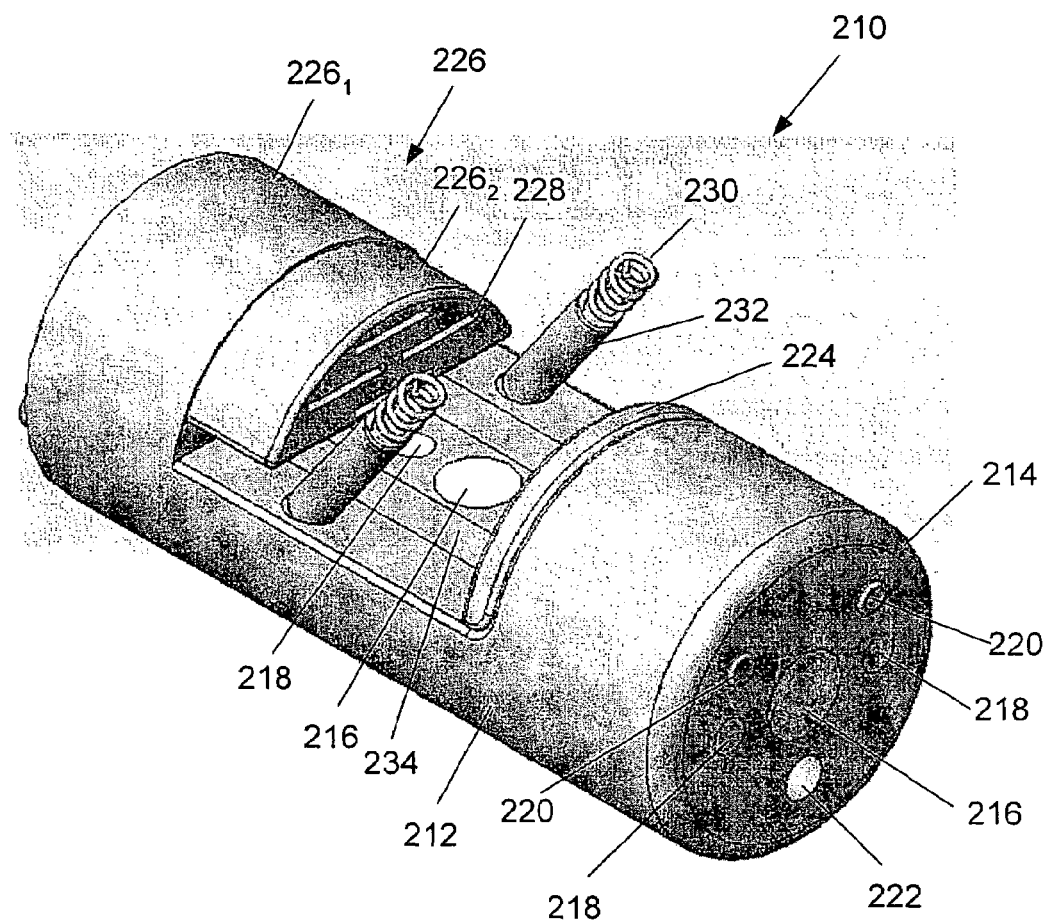
FIG. 11 is a general view from above showing the side closing embodiment of the stapler of the invention located in the distal tip of an endoscope.

FIG. 11 is a general view from above showing the side closing embodiment of the stapler 210 of the invention located in the distal tip 212 of an endoscope. On the distal face 214 can be seen a camera 216; the ends of two optic fibers 218, which provide light to illuminate the field of view of the camera; two nozzles 220 to spray air or water to keep the camera lens clean; and a working channel 222, which can be used to introduce other devices, e.g. ultrasound probe, forceps, etc. Experienced persons will recognize that the configuration and type of elements shown on the distal face in the figures is illustrative only, is not crucial to the present invention, and is related to the particular procedure to be performed and to the accessories provided.

Suitable cameras for use with the stapling device are described in WO2005/002210 and WO2005/115221. Cameras that are based on CMOS technology can be manufactured at a cost that is low enough to allow them to be discarded after a single use.

Stapler 210 is comprised of two components: the anvil 224, which is a semicircular flat surface at the bottom of which are attached two legs 234, a staple cartridge 226, which contains an array of staples that exit through slots 228 when the stapler is activated as described hereinbelow. The stapler cartridge is composed of two sections: a proximal section $226_1$, which is either fixedly attached to or manufactured as an integral part of the distal tip, and a distal section $226_2$, which can be slid into proximal section $226_1$ by pushing on the distal face of section $226_2$. In the side closing embodiment of stapler 210 the cartridge 226 and anvil 224 are located at the proximal and distal ends respectively of a recess cut into the side of distal tip 210. On the floor of the recess are located a camera 216, one or more light fibers 218, and water or air nozzles 220 in order to visualize the hole and the tissue grasping procedure as well as to inspect the tissue after the staples are ejected from the cartridge. In order to grasp the tissue, there are provided two screws 230 comprised of stiff wire bent into a spiral shape. The screws 230 pass through overtubes 232 located in channels through the insertion tube of the endoscope. They can be independently advanced, withdrawn, and rotated about their longitudinal axis from the handle at the proximal end of the endoscope.

Figure 12:
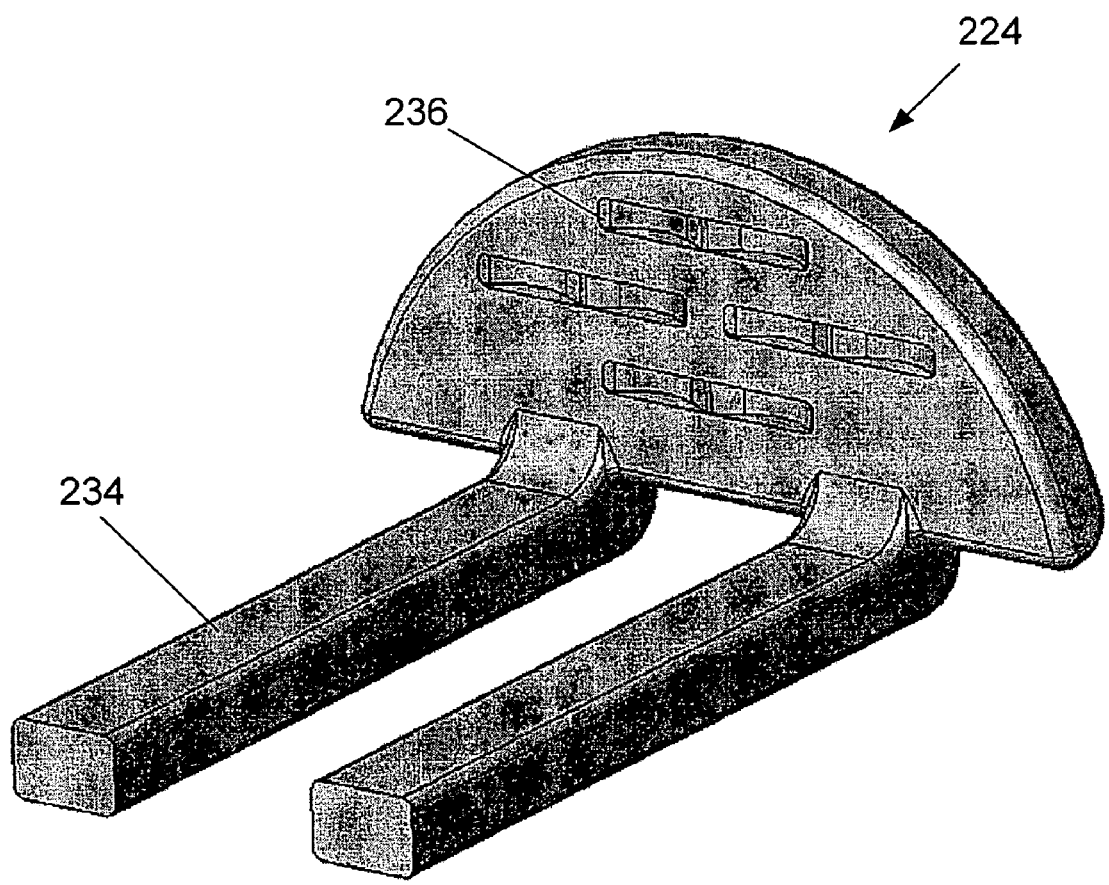
FIG. 12 shows the anvil removed from the endoscope.
Figure 14:
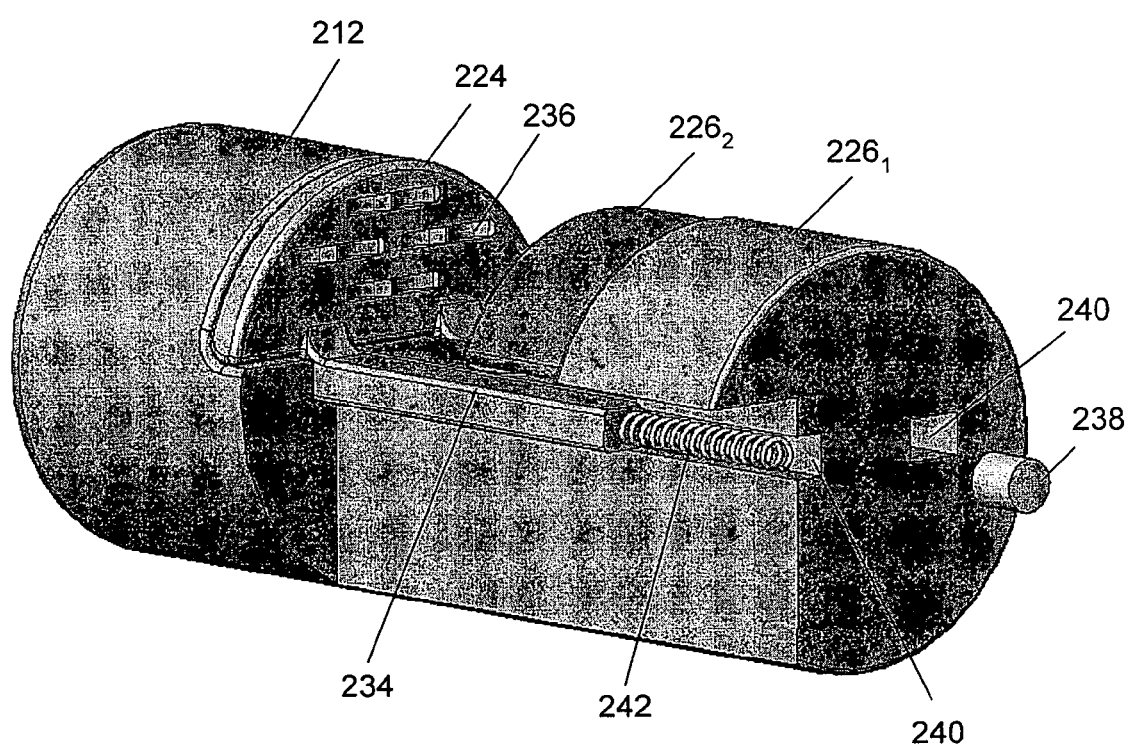

FIG. 12 shows the anvil 224 removed from the endoscope. In the figure the depressions 236 into which the legs of the staples enter and are curled when the staples are ejected from the stapler are seen on the face of the anvil. The stapler can be designed to utilize different sizes of staples depending on the diameter of the endoscope and properties of the tissue to be fastened. Typical standard sizes that can be used are 2, 2.5, 3, 3.3, and 4.8 mm staples. In FIGS. 11 and 12, the diameter of the endoscope is 12-15 mm and the stapler comprises an array of four 4.8 mm staples. FIG. 14 shows the same endoscope to which is fitted a stapler comprising an array of eight 2 mm staples.

Figure 13:
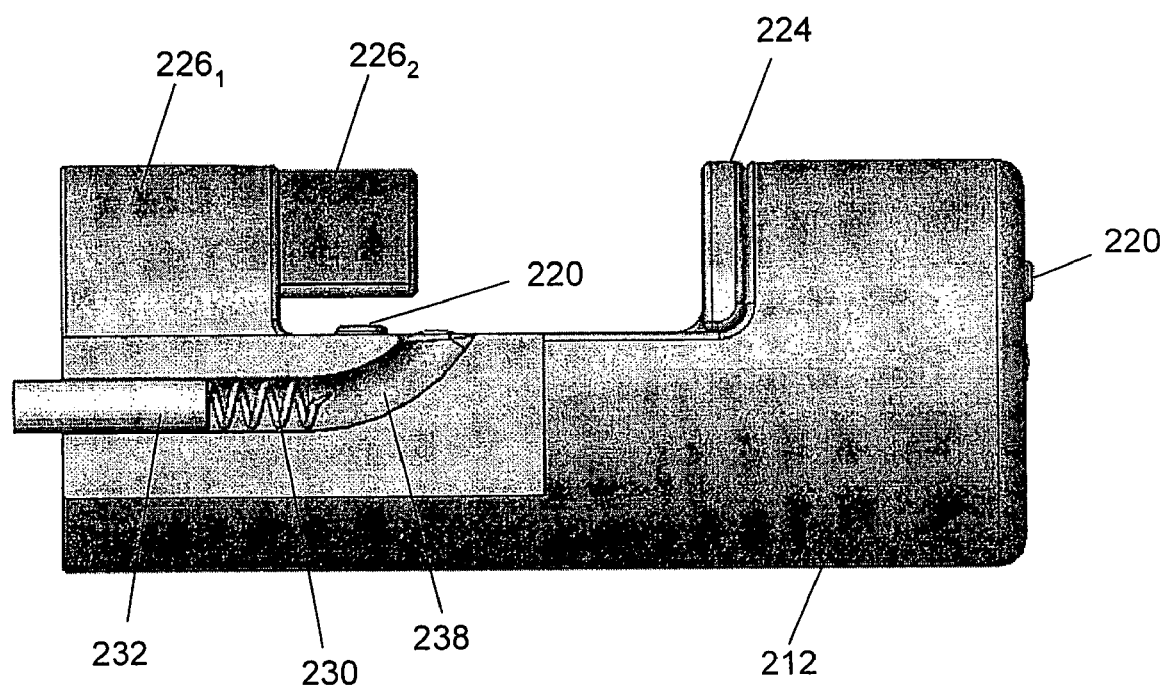
FIG. 13 and FIG. 14 are views with parts of the of the surface removed to reveal details of the interior of the distal tip.

FIG. 13 and FIG. 14 are views with parts of the surface removed to reveal details of the interior of the distal tip 212. In FIG. 13 can be seen the channel 238, through which the overtube 232 and enclosed screw 230 are advanced through the length of the endoscope. In FIG. 14 can be seen the channels 240 in which the legs 234 of the anvil can slide. Not shown in FIG. 14 is a cable that is attached to the proximal end of each leg 234, passes through the center of spring 242, and then passes through a channel in the insertion tube of the endoscope to the handle where its proximal end is attached to a mechanism that can be used to pull the entire anvil 224 in a proximal direction. When anvil 224 is pulled in a proximal direction, the proximal end of spring 242 butts up against a stopper (not shown) and is compressed. When the tension on the cable used to pull the anvil proximally is released, spring 242 pushes anvil 224 in the distal direction.

Figure 15:
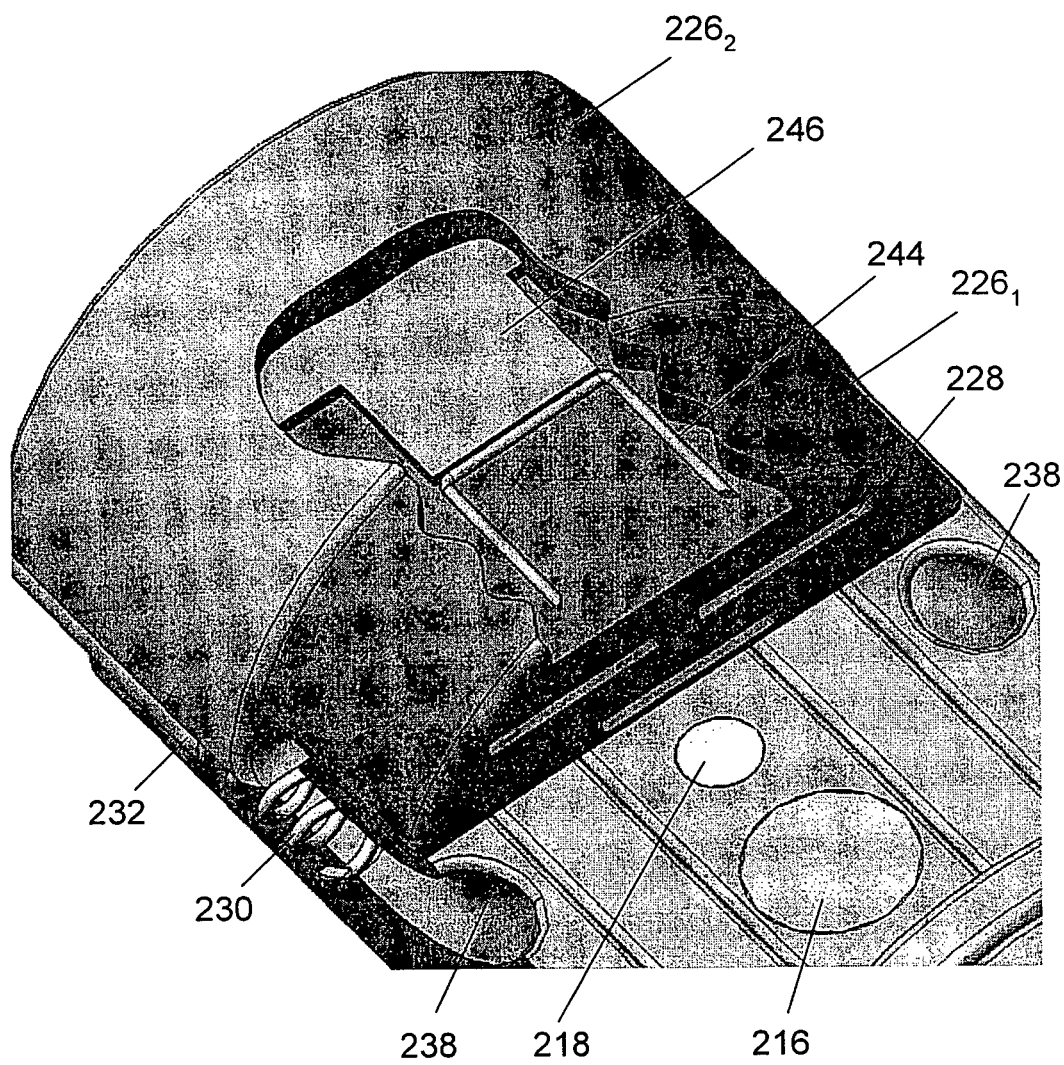
FIG. 15 is a view with part of the wall of the staple cartridge removed to reveal its interior.

FIG. 15 is a top view with part of the wall of the staple cartridge 226 removed to reveal its interior. The cartridge 226 of the stapler of the invention does not comprise any arrangement of cams to actively fire the staples. When the anvil 224 is pulled proximally as described herein above, the face of anvil 224 engages the face of cartridge 226 and pushes distal section $226_2$ proximally causing it to slide into proximal section $226_1$. Neither the staple pushers 246 nor the staples 244 move. The staple pushers merely act as a backstop to prevent staples 244 from moving in the proximal direction. In this way the legs of staples 244 are passively forced to exit the distal part $226_2$ of the cartridge through slots 228 and engage the matching depressions 236 on the face of anvil 234. Continued pulling on the cables attached to the legs 234 of the anvil 236 cause more and more of the length of the staples 244 to exit through slots 228 and the legs of the staples start to curl. The process continues until the staples 244 completely exit the cartridge 226 and the stapling process is completed. The cartridge 226 may contain one or more springs to provide a gradually yielding counter force to that exerted by the anvil, thereby aiding to provide a smooth exit of the staples and, if necessary, to return distal section $226_2$ to its original position as the anvil moves in the distal direction.

FIGS. 16A to 16F schematically show different stages in the operation of the side fastening embodiment of the stapler to close a hole in biological tissue.

Figure 16A:
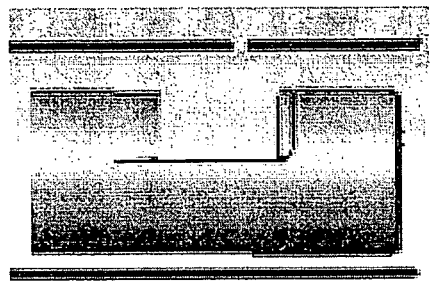
FIGS. 16A to 16F schematically show different stages in the operation of the side fastening embodiment of the endoscopic stapler used to close a hole in biological tissue.

The procedure is as follows:

FIG. 16A—The endoscope is inserted into the body cavity using the camera 216 on the distal face 214 for visualization until the hole in the tissue is viewed using the side facing camera 216.

Figure 16B:
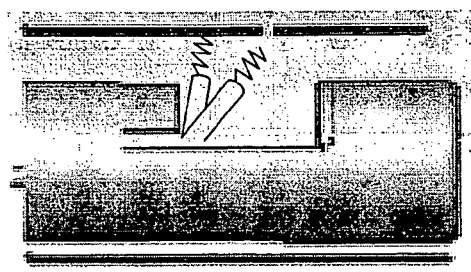

FIG. 16B—The sheaths 232 are pushed out of the channels 238 and the screws 230 are advanced and rotated until they penetrate and grab the tissue on opposite sides of the hole.

Figure 16C:
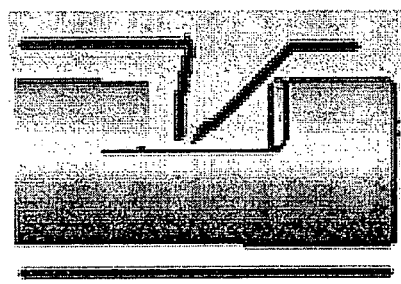

FIG. 16C—The sheaths 232 and the screws 230 with the tissue attached are pulled back into channels 238.

Figure 16D:
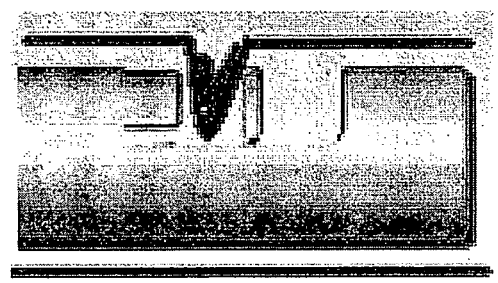

FIG. 16D—The cables attached to the legs 234 of the anvil 224 are pulled causing anvil 224 to move towards cartridge 226.

Figure 16E:
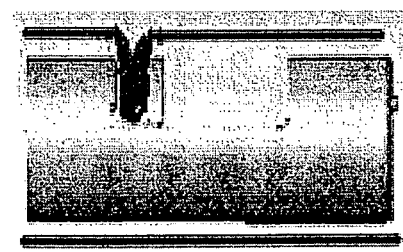

FIG. 16E—The tissue is compressed between the faces of the anvil 224 and the cartridge 226 and moveable cartridge section $226_2$ begins to slide into fixed cartridge section $226_1$. The legs of staples 244 begin to exit the slots 228, penetrate the layers of tissue and curl in the depressions 236.

Figure 16F:
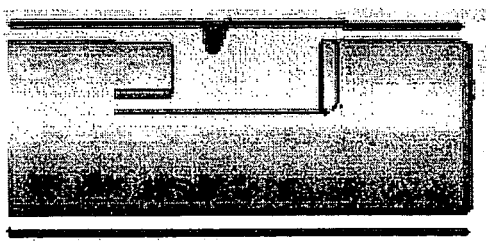

FIG. 16F—The stapling has been completed, screws 230 have been rotated to release their grip on the tissue, the cables attached to legs 234 have been released, and springs 242 have pushed the anvil 224 back to its original position, thereby freeing the stapled tissue. The closed hole is now inspected using the side viewing camera 216 and the endoscope can be withdrawn. If the hole is a large one, another endoscope containing a stapler of the invention can be introduced to the site of the hole and the same procedure followed again to apply a second array of staples next to the first array.

Figure 19:
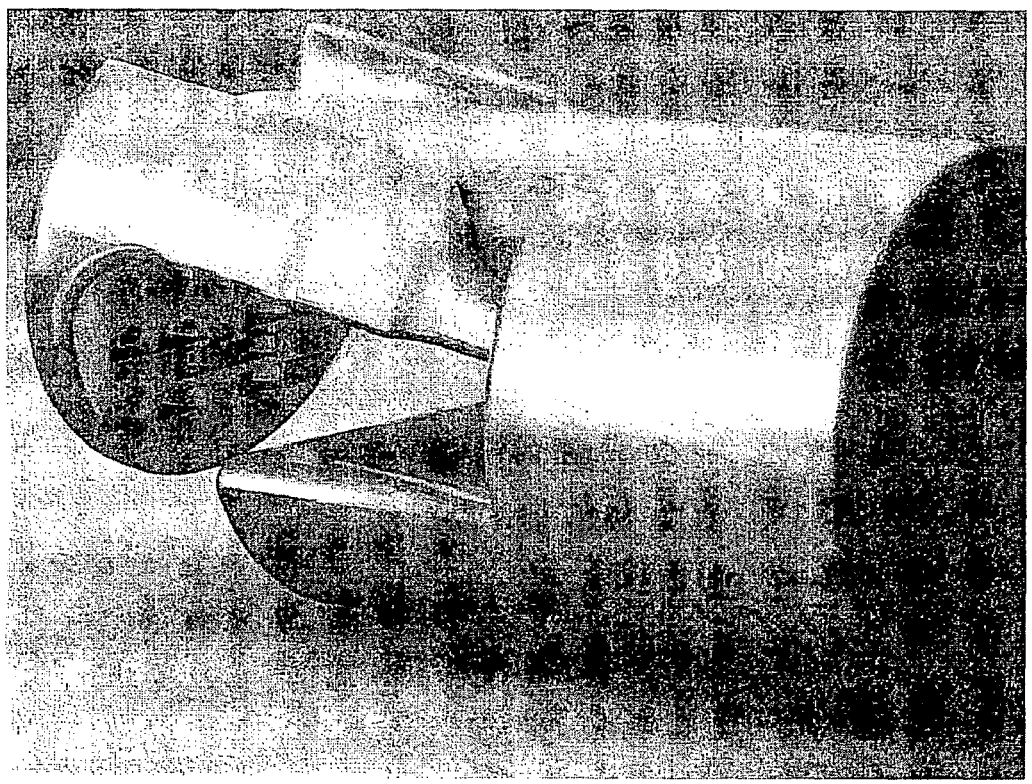

FIG. 17 to FIG. 19 show the front fastening embodiment of the stapler of the invention. Most of the components of the stapler according to this embodiment and its operation are the same as for the side fastening embodiment mutatis mutandis and will not be further described. The major difference between the two embodiments being that in the front fastening embodiment a mechanism activated from the operating handle of the endoscope, e.g. a spring loaded cam system, must be provided to raise and lower the anvil to enable the tissue to be grabbed and pulled between the faces of the anvil and the cartridge for stapling.

FIGS. 20A to 20F schematically show different stages in the operation of the front fastening embodiment of the stapler to close a hole in biological tissue. The procedure is as follows:

FIG. 20A—With the anvil lowered, the endoscope is inserted into the body cavity using the camera 16 on the distal face 214 for visualization. The endoscope is advanced and steered until the hole in the tissue is viewed directly in front of the camera.

FIG. 20B—the mechanism is activated from the control handle of the endoscope causing the anvil to be pushed out of the distal end;

FIG. 20C—as the anvil continues to advance out of the end of the endoscope, it gradually opens;

FIG. 20D—The sheaths 232 are pushed out of the channels 238 and the screws 230 are advanced and rotated until they penetrate and grab the tissue on opposite sides of the hole.

FIG. 20E—The sheaths 232 and the screws 230 with the tissue attached are pulled back into channels 238, the anvil is pulled distally towards the face of the cartridge forcing the anvil down into its lowered position, the tissue is compressed between the faces of the anvil 224 and the face of cartridge 226, moveable cartridge section $226_2$ begins to slide into fixed cartridge section $226_1$, the legs of staples 244 begin to exit the slots 228 penetrate the layers of tissue and curl in the depressions 236.

FIG. 20F—The stapling has been completed, screws 230 have been rotated to release their grip on the tissue, the anvil 224 is returned to its open position, thereby freeing the stapled tissue. The closed hole is now inspected using the camera 216 and the endoscope can be withdrawn. If the hole is a large one, another endoscope containing a stapler of the invention can be introduced to the site of the hole and the same procedure followed again to apply a second array of staples next to the first array.

Although embodiments of the invention have been described by way of illustration, it will be understood that the invention may be carried out with many variations, modifications, and adaptations, without exceeding the scope of the claims.

The invention claimed is:

1. A transgastric method for the endoscopic partial fundoplication for the treatment of gastroesophageal reflux disease (GERD) using an endoscope comprising an articulation section, a staple cartridge located proximally of said articulation section, a stapler anvil unit located distally of said articulation section, and an ultrasound positioning system; said method comprising the steps:
    (a) introducing the endoscope through the mouth and esophagus into the stomach of the patient;
    (b) using an endoscopic scalpel to cut a hole in the wall of said stomach;
    (c) pushing said endoscope through said hole;
    (d) using forceps to grab the tissue at a location on the outer surface of said stomach and moving said grabbed tissue closer to said esophagus;
    (e) positioning said staple cartridge in said esophagus;
    (f) making final adjustments prior to firing the staples;
    (g) firing said staples;
    (h) releasing said endoscope from its firing configuration;
    (i) removing said endoscope from the body of said patient; and
    (j) using staples to close said hole.

2. A method according to claim 1, wherein between step (h) and step (i) the endoscope is rotated one or more times and after each rotation steps (d) to (h) are repeated at a different location.

3. A method according to claim 1, wherein the hole is made in the upper anterior wall of the stomach near to the greater curvature of said stomach.

4. A method according to claim 2, wherein the endoscope is rotated two times, by 90 to 100 degrees each time, and the different locations at which the tissue is grabbed are:
    (a) the exterior of the fundus;
    (b) the exterior of the anterior wall; and
    (c) the exterior wall of the stomach on or near the lesser curvature.

5. A method according to claim 1, wherein step (a) comprises:
    (a) activating visualization means located on the endoscope to be able to observe the stages of the procedure;
    (b) introducing said endoscope in its straightened configuration through the mouth and the esophagus of the patient into the stomach;
    (c) partially bending the articulation section after the distal end of said endoscope enters the interior of said stomach; and
    (d) guiding the distal face of said endoscope to a location close to the anterior wall near the greater curvature of said stomach.

6. A method according to claim 1, wherein step (b) comprises:
    (a) cutting the hole in the anterior wall by means of the endoscopic scalpel that is guided to the site through the working channel of the endoscope; and
    (b) withdrawing said endoscopic scalpel from said working channel after said hole is made.

7. A method according to claim 1, wherein step (c) comprises:
    (a) pushing the distal tip of the endoscope through the hole to the outside of the stomach; and
    (b) further advancing said endoscope distally and bending the articulation section until the distal tip is close to the outer wall of said stomach.

8. A method according to claim 1, wherein step (d) comprises:
    (a) grabbing the tissue on the outer wall of the stomach with the forceps that is passed through the working channel and exits the distal face of the endoscope; and
    (b) further bending and moving the articulation section until said grabbed tissue is pulled close to the outer wall of the esophagus.

9. A method according to claim 1, wherein step (e) comprises:
    (a) moving the curved endoscope as necessary until the stapler cartridge is located in the esophagus a distance about three centimeters above the LES and rotated until the stapler cartridge faces the direction of the greater curvature of the stomach; and
    (b) locking said endoscope in position.

10. A method according to claim 1, wherein step (f) comprises:
    (a) activating the ultrasound positioning system to aid in final alignment of the stapler anvil unit with the cartridge;
    (b) advancing locking screws out of the anvil unit and into bores in the staple cartridge;
    (c) halting the action of the mechanism that advances said screws when the signals from said ultrasound system indicate that the proper distance between the faces of said anvil and said staple cartridge has been achieved;
    (d) releasing the hold of the forceps on the tissue of the stomach and retracting said forceps into the working channel; and
    (e) making a final visual and ultrasonic confirmation that the endoscope is in the proper position and that said anvil and said cartridge are in the correct working relationship.

11. A method according to claim 1, wherein step (h) comprises:

(a) loosening the locking screws and visually inspecting the area to verify that the legs of the staples have properly curled and that the tissue is fastened correctly;
(b) totally withdrawing said screws into the anvil unit;
(c) partially unbending the articulation section; and
(d) unlocking the endoscope 12. A method according to claim 1, wherein the staples used to close the hole are replaced by one or more of the following:
(a) sutures;
(b) clips; or
(c) biological glue.

13. A method according to claim 1, wherein the endoscopic scalpel is replaced by one of the following:
(a) a RF cutter;
(b) a laser; or
(c) an ultrasonic cutter.

14. A method according to claim 1, wherein the forceps are replaced by a screw comprised of stiff wire bent into a spiral shape.

15. A method according to claim 9, wherein the endoscope is locked in position by means of locking screws provided in a bite block located in the patient's mouth.

16. A method according to claim 1, wherein, in step (j), the staples are applied by means of a dedicated endoscopic stapling device especially designed for the task of closing holes in tissue.

17. A method according to claim 16, wherein the dedicated endoscopic stapling device is discarded after a single use.

18. A method according to claim 8, wherein the forceps are replaced by a screw comprised of stiff wire bent into a spiral shape.

19. A method according to claim 10, wherein the forceps are replaced by a screw comprised of stiff wire bent into a spiral shape.

* * * * *